(12) United States Patent
Wityak et al.

US008536186B2

(10) Patent No.: US 8,536,186 B2
(45) Date of Patent: Sep. 17, 2013

(54) CERTAIN KYNURENINE-3-MONOOXYGENASE INHIBITORS, PHARMACEUTICAL COMPOSITIONS, AND METHODS OF USE THEREOF

(75) Inventors: John Wityak, Carlsbad, CA (US); Leticia M. Toledo-Sherman, Santa Monica, CA (US); Celia Dominguez, Los Angeles, CA (US); Stephen Martin Courtney, Oxfordshire (GB); Christopher John Yarnold, Oxfordshire (GB); Paula C. De Aguiar Pena, Oxfordshire (GB); Andreas Scheel, Hamburg (DE); Dirk Winkler, Hamburg (DE)

(73) Assignee: CHDI Foundation, Inc., New York, NY (US)

( * ) Notice: Subject to any disclaimer, the term of this patent is extended or adjusted under 35 U.S.C. 154(b) by 20 days.

(21) Appl. No.: 13/056,305

(22) PCT Filed: Aug. 4, 2009

(86) PCT No.: PCT/US2009/052667
§ 371 (c)(1),
(2), (4) Date: Apr. 13, 2011

(87) PCT Pub. No.: WO2010/017179
PCT Pub. Date: Feb. 11, 2010

(65) Prior Publication Data
US 2011/0183957 A1 Jul. 28, 2011

Related U.S. Application Data

(60) Provisional application No. 61/086,090, filed on Aug. 4, 2008.

(51) Int. Cl.
*A01N 43/54* (2006.01)
*C07D 239/42* (2006.01)
*C07D 401/04* (2006.01)

(52) U.S. Cl.
USPC .......................... 514/256; 544/334; 544/335

(58) Field of Classification Search
USPC .......................................................... 544/335
See application file for complete search history.

(56) References Cited

U.S. PATENT DOCUMENTS

| 5,064,832 | A | 11/1991 | Stanek et al. | |
| 5,439,912 | A | 8/1995 | Hubele | |
| 6,194,428 | B1 | 2/2001 | Urbahns et al. | |
| 6,455,520 | B1 * | 9/2002 | Brown et al. | 514/217.11 |
| 7,049,318 | B2 | 5/2006 | Dominguez et al. | |
| 7,105,549 | B2 | 9/2006 | Shao et al. | |
| 7,345,178 | B2 | 3/2008 | Nunes et al. | |
| 7,947,680 | B2 * | 5/2011 | Jimenez et al. | 514/235.5 |
| 8,198,275 | B2 * | 6/2012 | Jimenez et al. | 514/235.5 |
| 2002/0049207 | A1 | 4/2002 | McCarthy | |
| 2005/0288308 | A1 * | 12/2005 | Amrien et al. | 514/256 |
| 2006/0189806 | A1 | 8/2006 | Bernardini et al. | |
| 2006/0223849 | A1 | 10/2006 | Mjalli et al. | |
| 2007/0060573 | A1 * | 3/2007 | Wortmann et al. | 514/218 |
| 2008/0058391 | A1 | 3/2008 | Johnson et al. | |
| 2008/0187575 | A1 | 8/2008 | Klebl et al. | |
| 2008/0188452 | A1 | 8/2008 | Altenbach et al. | |
| 2010/0022546 | A1 * | 1/2010 | Jimenenz et al. | 514/237.2 |
| 2011/0015232 | A1 | 1/2011 | Charest et al. | |
| 2011/0178086 | A1 * | 7/2011 | Jimenez et al. | 514/235.5 |
| 2011/0183957 | A1 | 7/2011 | Wityak et al. | |

FOREIGN PATENT DOCUMENTS

| EP | 1 679 309 A1 | 7/2006 |
| EP | 1 783 116 B1 | 5/2007 |
| EP | 1 928 842 B1 | 6/2008 |
| JP | 2007-230963 | 9/2007 |
| JP | 2009-280521 | 12/2009 |
| WO | WO-02/060877 A1 | 8/2002 |
| WO | WO-03/002536 A1 | 1/2003 |
| WO | WO-03/022276 A1 | 3/2003 |
| WO | WO-03/066623 A1 | 8/2003 |
| WO | WO-2004/014844 A2 | 2/2004 |
| WO | WO-2004/032933 A1 | 4/2004 |
| WO | WO-2005/003123 A1 | 1/2005 |
| WO | WO-2005/042498 A2 | 5/2005 |
| WO | WO-2006/062093 A1 | 6/2006 |
| WO | WO-2006/086600 A1 | 8/2006 |
| WO | WO-2007/017289 A2 | 2/2007 |

(Continued)

OTHER PUBLICATIONS

International Preliminary Report on Patentability, PCT/US09/52667 (Feb. 8, 2011).*
B Testa et al., Prodrug Design in, 5 Encyclopedia of Pharmaceutical Technology, 3008-3014 (J. Swarbrick ed., 3rd ed., 2007).*
T. Sakamoto et al., 28 Chemical & Pharmaceutical Bulletin 202-207 (1980).*
P. Molina et al., 34 Tetrahedron Letters 3773-3776 (1993).*
Berthel, et al., "Identification of phenyl-pyridine-2-carboxylic acid derivatives as novel cell cycle inhibitors with increased selectivity for cancer cells." Anti-Cancer Drugs, 13:359-366 (2002).

(Continued)

*Primary Examiner* — James O Wilson
*Assistant Examiner* — Alexander R Pagano

(57) ABSTRACT

Certain chemical entities are provided herein. Also provided are pharmaceutical compositions comprising at least one chemical entity and one or more pharmaceutically acceptable vehicle. Methods of treating patients suffering from certain diseases and disorders responsive to the inhibition of KMO activity are described, which comprise administering to such patients an amount of at least one chemical entity effective to reduce signs or symptoms of the disease or disorder are disclosed. These diseases include neurodegenerative disorders such as Huntington's disease. Also described are methods of treatment include administering at least one chemical entity as a single active agent or administering at least one chemical entity in combination with one or more other therapeutic agents. Also provided are methods for screening compounds capable of inhibiting KMO activity.

6 Claims, No Drawings

(56) References Cited

FOREIGN PATENT DOCUMENTS

| WO | WO-2007/019416 A1 | 2/2007 |
|---|---|---|
| WO | WO-2007/024922 A1 | 3/2007 |
| WO | WO-2007/067836 A2 | 6/2007 |
| WO | WO-2007/070818 A1 | 6/2007 |
| WO | WO 2007070818 A1 * | 6/2007 |
| WO | WO-2007/093542 A1 | 8/2007 |
| WO | WO-2008/002576 A2 | 1/2008 |
| WO | WO-2008/022286 A2 | 2/2008 |
| WO | WO-2008/023720 A1 | 2/2008 |
| WO | WO-2008/034008 A2 | 3/2008 |
| WO | WO-2008/095852 A1 | 8/2008 |
| WO | WO-2008/121877 A2 | 10/2008 |
| WO | WO-2008/152099 A2 | 12/2008 |
| WO | WO-2009/006389 A2 | 1/2009 |
| WO | WO-2009/082346 A1 | 7/2009 |
| WO | WO-2009/148004 A1 | 12/2009 |
| WO | WO-2010/005783 A1 | 1/2010 |
| WO | WO-2010/017179 A1 | 2/2010 |
| WO | WO-2010/100475 A1 | 9/2010 |
| WO | WO-2010/117323 A1 | 10/2010 |
| WO | WO-2010/134478 A1 | 11/2010 |
| WO | WO-2011/008709 A1 | 1/2011 |
| WO | WO-2011/046771 A1 | 4/2011 |
| WO | WO-2011/050323 A1 | 4/2011 |
| WO | WO-2011/091153 A1 | 7/2011 |
| WO | WO 2011091153 A1 * | 7/2011 |
| WO | WO-2011/104322 A1 | 9/2011 |
| WO | WO-2012/003387 A1 | 1/2012 |
| WO | WO-2012/035421 A2 | 3/2012 |

OTHER PUBLICATIONS

Bredereck, et al., "Foramid-Reaktionen, VIII. Eine neue pyrimidin-synthese." Chemische Berichte 90:942-52 (1957).
Chatterjea, et al., "Synthesis in 3-azafluorene group. Part III." J. Indian Chem. Soc., vol. LXI, 1028-1031 (1984).
Chemical Abstracts Service. CAS Reg. No. 1017484-83-1 (Apr. 27, 2008).
Chemical Abstracts Service. CAS Reg. No. 1017484-87-5 (Apr. 27, 2008).
Chemical Abstracts Service. CAS Reg. No. 1017484-91-1 (Apr. 27, 2008).
Chemical Abstracts Service. CAS Reg. No. 1017484-95-5 (Apr. 27, 2008).
Chemical Abstracts Service. CAS Reg. No. 1017394-18-1 (Apr. 25, 2008).
Chemical Abstracts Service. CAS Reg. No. 1017396-21-2 (Apr. 25, 2008).
Chemical Abstracts Service. CAS Reg. No. 1017396-26-7 (Apr. 25, 2008).
Chemical Abstracts Service. CAS Reg. No. 1017396-31-4 (Apr. 25, 2008).
Chemical Abstracts Service. CAS Reg. No. 1017438-20-8 (Apr. 25, 2008).
Chemical Abstracts Service. CAS Reg. No. 1017438-24-2 (Apr. 25, 2008).
Chemical Abstracts Service. CAS Reg. No. 1017438-28-6 (Apr. 25, 2008).
Chemical Abstracts Service. CAS Reg. No. 1017438-32-2 (Apr. 25, 2008).
Chemical Abstracts Service. CAS Reg. No. 1017438-36-6 (Apr. 25, 2008).
Chemical Abstracts Service. CAS Reg. No. 1017484-79-5 (Apr. 27, 2008).
Chemical Abstracts Service. CAS Reg. No. 1017484-99-9 (Apr. 27, 2008).
Eglinton, et al.,"The chemistry of fungi. Part XXXV. A preliminary investigation of ergoflavin." View Online/Journal Homepage, 1833-1842 (1958).
EP Application No. 09805426. Suppl. Search Report dated Feb. 2, 2012.
Filosa, et al., "Synthesis and antiproliferative properties of N3/8-disubstituted 3,8-diazabicyclo[3.2.1]octane analogues of 3,8-bis[2-(3,4,5-trimethoxyphenyl)pyridine-4-yl]methyl-piperazine." Eur. J. Med. Chem. 42:293-306 (2007).
Han, et al., "Lead optimization studies on FimH antagonists: discovery of potent and orally bioavailable ortho-substituted biphenyl mannosides." J. Med. Chem. 55:3945-3959 (2012).
Kato et al., "The Vilsmeier reaction of methylpyrimidine derivatives." Yakugaku Zasshi 90(7):870-876 (1970).
Kobayashi, et al., "A novel strategy for the synthesis of 2-arylpyridines using one-pot 6 π-azaelectrocyclization." Tetrahedron Ltrs., 49:4349-4351 (2008).
Kort, et al., "Subtype-selective Nav1.8 sodium channel blockers: Identification of potent orally active nicotinamide derivatives." Bioorg. & Med. Chem. Ltrs. 20:6812-6815 (2010).
Kulkarni, et al., "Design and synthesis of novel heterobiaryl amides as metabotropic glutamate receptor subtype 5 antagonists." Bioorg. & Med. Chem. Ltrs. 17:2074-2079 (2007).
Li, et al., "Discovering novel chemical inhibitors of human cyclophilin A: virtual screening, synthesis, and bioassay." Bioorganic & Medicinal Chemistry, 14:2209-2224 (2006).
Molina, et al., "Electrocyclization of 3-azahexa-1,3,5-trienes: a convenient iminophosphorane-mediated preparation of 4-arylpyridines." Tetrahedron Ltrs. 34(23):3773-3776 (1993).
Osborne et al., "The chemistry of triazine derivatives II. The acylation of 2,4,6-trimethyl-s-triazine to triazinyl ketones and their facile isomerization to acetamidopyrimidines." J. Heterocyclic Chem. 1.(Jul. 1, 1964) pp. 145-150 (1964).
PCT/US2009/052667. International Search Report & Written Opinion dated Oct. 13, 2009.
PCT/US2011/021890. International Search Report dated Mar. 29, 2011.
Pratsch, et al., "Hydroxy- and aminophenyl radicals from arenediazonium salts." Chem. Eur. J. 17:4104-4108 (2011).
Proctor, et al., "Bridged-ring nitrogen compounds. part 5,1 synthesis of 2,6-methano-3-benzazonine ring-systems." JCS Perkin I, 1754-1762 (1981).
Sakaguchi, et al., "Library-directed solution- and solid-phase synthesis of 2,4-disubstituted pyridines: one-pot approach through 6 π-azaelectrocyclization." Chem. Asian. J. 4:1573-1577 (2009).
Sakamoto, et al., "Studies on pyrimidine derivatives. XVI. site selectivity in the homolytic substitution of simple pyrimidines." Chem Pharm. Bull. 28(2):571-577 (1980).
Shao, et al., Phenoxyphenyl pyridines as novel state-dependent, high-potency sodium channel inhibitors. J. Med. Chem. 47:4277-4285 (2004).
van Muijlwijk-Koezen, et al., "Thiazole and thiadiazole analogues as a novel class of adenosine receptor antagonists." J. Med. Chem. 44:749-762 (2001).
Von Angerer, "Product class 12: pyrimidines." Science of Synthesis Houben-Weyl Methods of Molecular Transformations, Category 2, vol. 16 (2003).
Warshakoon, et al., "Design and synthesis of substituted pyridine derivatives as HIF-1α prolyl hydroxylase inhibitors." Bioorganic & Medicinal Chemistry Lett. 16:5616-5620 (2006).
Arzel, et al. A new synthesis of α-substituted δ-carbolines. Journal of Heterocyclic Chemistry vol. 34, Issue 4, pp. 1205-1210, 1997.
Database Registry, Chemical Library Supplier: Ambinte, Entered STN: Apr. 25, 2008.
PCT/US2012/48254. International Search Report & Written Opinion dated Sep. 24, 2012.
PCT/US2012/052617. International Search Report & Written Opinion dated Oct. 22, 2012.
Chemical Abstracts Service. CAS Reg. No. 52565-56-7 (1984), 1 p.
Chemical Abstracts Service. CAS Reg. No. 55240-51-2 (1984), 1p.
Chemical Abstracts Service. CAS Reg. No. 887407-77-4 (2006), 1 p.

* cited by examiner

CERTAIN KYNURENINE-3-MONOOXYGENASE INHIBITORS, PHARMACEUTICAL COMPOSITIONS, AND METHODS OF USE THEREOF

CROSS-REFERENCE TO RELATED APPLICATIONS

This application claims the benefit under 35 U.S.C. §371 of PCT International Application No. PCT/US2009/052667, filed Aug. 4, 2009, which in turn claims priority to U.S. Provisional Application No. 61/086,090, filed Aug. 4, 2008, the contents of each which are hereby incorporated by reference in their entirety.

Provided herein are certain kynurenine-3-monooxygenase inhibitors, pharmaceutical compositions thereof; and methods of their use.

Kynurenine-3-monooxygenase (KMO) is an enzyme in the tryptophan degradation pathway that catalyzes the conversion of kynurenine into 3-hydroxykynurenine (3-HK), which is a precursor of the neurotoxin quinolinic acid (QUIN). Therefore, compounds which act as inhibitors of KMO are of particular interest since they may block the metabolism toward QUIN and at the same time, may increase the formation of neuroprotective metabolite kynurenic acid (KYNA).

KMO inhibitors have been proposed as therapeutic agents for the treatment of neurodegenerative disease such Huntington's disease, Alzheimer's disease, dementia caused by Acquired Immunodeficiency Syndrome (AIDS), infarctual dementia, cerebral ischemia, cerebral hypoxia, Parkinson's disease, epilepsy, head and spinal cord injury, amyotrophic lateral sclerosis, glaucoma retinopathy, infections of the brain or inflammations of the brain. There remains a need for compounds that are effective inhibitors of KMO and may be used in treating neurodegenerative disorders.

Provided is at least one chemical entity chosen from compounds of Formula I

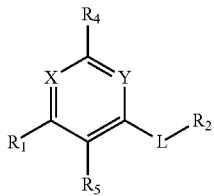

Formula I and pharmaceutically acceptable salts and prodrugs thereof wherein:

X and Y are independently chosen from CH and N provided that at least one of X and Y is N;

$R_1$ is chosen from aryl and heteroaryl, each of which is substituted with one, two, or three groups chosen from halo, optionally substituted lower alkyl, lower alkoxy, optionally substituted amino, optionally substituted heterocycloalkyl, optionally substituted heteroaryl, and hydroxy;

L is chosen from —C(O)O—, —C(O)N($R_3$)—, —N($R_3$)C(O)—, —N($R_3$)S(O)$_2$—, and —S(O)$_2$N($R_3$)—;

$R_2$ is chosen from hydrogen, optionally substituted lower alkyl, optionally substituted aryl, optionally substituted heteroaryl, optionally substituted cycloalkyl, and optionally substituted heterocycloalkyl, provided that when L is —N($R_3$)S(O)$_2$— $R_2$ is not hydrogen;

$R_3$ is chosen from hydrogen and lower alkyl; or $R_2$ and $R_3$, taken together with any intervening atoms, forms an optionally substituted heterocycloalkyl ring;

$R_4$ is chosen from hydrogen and optionally substituted lower alkyl; and $R_5$ is chosen from hydrogen and fluoro, provided that the compound of Formula I is not N-(1-hydroxy-3-(1H-indol-3-yl)propan-2-yl)-6-(4-methoxyphenyl)pyrimidine-4-carboxamide;

3-chloro-2-methyl-N-(6-phenylpyrimidin-4-yl)benzenesulfonamide;

4-methoxy-N-(6-phenylpyrimidin-4-yl)benzamide;

N-(6-phenylpyrimidin-4-yl)benzamide;

6-phenylpyrimidine-4-carboxylic acid;

methyl 6-phenylpyrimidine-4-carboxylate;

ethyl 6-phenylpyrimidine-4-carboxylate;

6-phenylpyrimidine-4-carboxamide;

N-methyl-6-phenylpyrimidine-4-carboxamide; or

N,N-dimethyl-6-phenylpyrimidine-4-carboxamide.

Also provided is a pharmaceutical composition comprising at least one chemical entity described herein and at least one pharmaceutically acceptable excipient.

Also provided is a packaged pharmaceutical composition comprising at least one pharmaceutical composition described herein and instructions for using the composition to treat a subject suffering from a condition or disorder mediated by Kynurenine 3-mono-oxygenase activity.

Also provided is a method of treating a condition or disorder mediated by Kynurenine 3-mono-oxygenase activity in a subject in need of such a treatment which method comprises administering to the subject a therapeutically effective amount of at least one chemical entity described herein.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 4 carbons.

"Aryl" encompasses:
  5- and 6-membered carbocyclic aromatic rings, for example, benzene;
  bicyclic ring systems wherein at least one ring is carbocyclic and aromatic, for example, naphthalene, indane, and tetralin; and
  tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "halo" includes fluoro, chloro, bromo, and iodo, and the term "halogen" includes fluorine, chlorine, bromine, and iodine.

"Heteroaryl" encompasses:
  5- to 7-membered aromatic, monocyclic rings containing one or more, for example, from 1 to 4, or In some embodiments, from 1 to 3, heteroatoms chosen from N, O, and S, with the remaining ring atoms being carbon; and
  bicyclic heterocycloalkyl rings containing one or more, for example, from 1 to 4, or In some embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For example, heteroaryl also includes a 5- or 6-membered heterocycloalkyl, aromatic ring fused to a 5- to 7-membered aryl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide (—O$^-$) substituents, such as pyridinyl N-oxides.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. "Heterocycloalkyl" also refers to 5- and 6-membered carbocyclic aromatic rings fused to a 5- to 7-membered heterocycloalkyl ring containing 1 or more heteroatoms chosen from N, O, and S, provided that the point of attachment is at the heterocycloalkyl ring. Suitable heterocycloalkyl groups include, for example (as numbered from the linkage position assigned priority 1), 2-pyrrolidinyl, 2,4-imidazolidinyl, 2,3-pyrazolidinyl, 2-piperidinyl, 3-piperidinyl, 4-piperidinyl, and 2,5-piperazinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation lower alkyl), cycloalkyl, aryl (including without limitation phenyl), heterocycloalkyl (including without limitation morpholin-4-yl, 3,4-dihydroquinolin-1(2H)-yl, indolin-1-yl, 3-oxopiperazin-1-yl, piperidin-1-yl, piperazin-1-yl, pyrrolidin-1-yl, azetidin-1-yl, and isoindolin-2-yl), and heteroaryl (including without limitation pyridinyl), unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —$O(C_1-C_2$ alkyl)$O$— (e.g., methylenedioxy-), —$SR^b$, guanidine, guanidine wherein one or more of the guanidine hydrogens are replaced with a lower-alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from optionally substituted $C_1-C_6$ alkyl, optionally substituted cycloalkyl, optionally substituted aryl, optionally substituted heterocycloalkyl, and optionally substituted heteroaryl;

$R^b$ is chosen from H, optionally substituted $C_1-C_6$ alkyl, optionally substituted aryl, and optionally substituted heteroaryl; and $R^c$ is chosen from hydrogen and optionally substituted $C_1-C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1-C_4$ alkyl, $C_3-C_6$ cycloalkyl, aryl, heteroaryl, aryl-$C_1-C_4$ alkyl-, heteroaryl-$C_1-C_4$ alkyl-, $C_1-C_4$ haloalkyl-, —$OC_1-C_4$ alkyl, —$OC_1-C_4$ alkylphenyl, —$C_1-C_4$ alkyl-OH, —$C_1-C_4$ alkyl-O—$C_1-C_4$ alkyl, —$OC_1-C_4$ haloalkyl, halo, —OH, —$NH_2$, —$C_1-C_4$ alkyl-$NH_2$, —$N(C_1-C_4$ alkyl)($C_1-C_4$ alkyl), —NH($C_1-C_4$ alkyl), —$N(C_1-C_4$ alkyl)($C_1-C_4$ alkylphenyl), —NH($C_1-C_4$ alkylphenyl), cyano, nitro, oxo (as a substitutent for heteroaryl), —$CO_2H$, —$C(O)OC_1-C_4$ alkyl, —$CON(C_1-C_4$ alkyl)($C_1-C_4$ alkyl), —$CONH(C_1-C_4$ alkyl), —$CONH_2$, —$NHC(O)(C_1-C_4$ alkyl), —NHC(O)(phenyl), —$N(C_1-C_4$ alkyl)C(O)($C_1-C_4$ alkyl), —$N(C_1-C_4$ alkyl)C(O)(phenyl), —$C(O)C_1-C_4$ alkyl, —$C(O)C_1-C_4$ phenyl, —$C(O)C_1-C_4$ haloalkyl, —$OC(O)C_1-C_4$ alkyl, —$SO_2$ ($C_1-C_4$ alkyl), —$SO_2$(phenyl), —$SO_2(C_1-C_4$ haloalkyl), —$SO_2NH_2$, —$SO_2NH$ ($C_1-C_4$ alkyl), —$SO_2NH$(phenyl), —$NHSO_2(C_1-C_4$ alkyl), —$NHSO_2$ (phenyl), and —$NHSO_2(C_1-C_4$ haloalkyl).

The term "substituted alkoxy" refers to alkoxy wherein the alkyl constituent is substituted (i.e., —O-(substituted alkyl)) wherein "substituted alkyl" is as described herein. "Substituted alkoxy" also includes glycosides (i.e., glycosyl groups) and derivatives of ascorbic acid.

The term "substituted amino" refers to the group —$NHR^d$ or —$NR^dR^d$ where each $R^d$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, optionally substituted alkoxycarbonyl, sulfinyl and sulfonyl, each as described herein, and provided that only one $R^d$ may be hydroxyl. The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Aminocarbonyl" encompasses a group of the formula —(C=O)(optionally substituted amino) wherein substituted amino is as described herein.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3$(C=O)—.

By "alkoxycarbonyl" is meant an ester group of the formula (alkoxy)(C=O)— attached through the carbonyl carbon wherein the alkoxy group has the indicated number of carbon atoms. Thus a $C_1-C_6$alkoxycarbonyl group is an alkoxy group having from 1 to 6 carbon atoms attached through its oxygen to a carbonyl linker.

By "amino" is meant the group —$NH_2$.

The term "sulfinyl" includes the groups: —S(O)-(optionally substituted ($C_1-C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —$S(O_2)$-(optionally substituted ($C_1-C_6$)alkyl), —$S(O_2)$-optionally substituted aryl), —$S(O_2)$-optionally substituted heteroaryl), —$S(O_2)$-(optionally substituted heterocycloalkyl), —$S(O_2)$-(optionally substituted alkoxy), —$S(O_2)$-optionally substituted aryloxy), —$S(O_2)$-optionally substituted heteroaryloxy), —$S(O_2)$-(optionally substituted heterocyclyloxy); and —$S(O_2)$-(optionally substituted amino).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxy" refers to alkoxy wherein the alkyl constituent is substituted (i.e., —O-(substituted alkyl)) wherein "substituted alkyl" is as described herein.

The term "substituted alkoxycarbonyl" refers to the group (substituted alkyl)-O—C(O)— wherein the group is attached to the parent structure through the carbonyl functionality and wherein substituted alkyl is as described herein.

"Glycosides" refer to any of a number of sugar derivatives that contain a non-sugar group bonded to an oxygen or nitrogen atom of a sugar and that on hydrolysis yield that sugar. An example of a glycosyl group is glucosyl.

"Derivatives of ascorbic acid" or "ascorbic acid derivatives" refer to any of a number of derivatives that contain a non-sugar group bonded to an oxygen or nitrogen atom of ascorbic acid and that on hydrolysis yield ascorbic acid (i.e., (R)-5-((S)-1,2-dihydroxyethyl)-3,4-dihydroxyfuran-2(5H)-one).

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-performance liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

Chemical entities include, but are not limited to compounds described herein and all pharmaceutically acceptable forms thereof. Pharmaceutically acceptable forms of the compounds recited herein include pharmaceutically acceptable salts, prodrugs, and mixtures thereof. In some embodiments, the compounds described herein are in the form of pharmaceutically acceptable salts and prodrugs. Hence, the terms "chemical entity" and "chemical entities" also encompass pharmaceutically acceptable salts, prodrugs, and mixtures thereof.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities described herein. In some embodiments, the "prodrugs" described herein include any compound that becomes a compound of Formula I when administered to a patient, e.g., upon metabolic processing of the prodrug. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as $NHR^x$, and $NR^xR^y$, wherein $R^x$ is hydrogen, $(C_1-C_{18})$-alkyl, $(C_3-C_7)$-cycloalkyl, $(C_3-C_7)$-cycloalkyl-$(C_1-C_4)$-alkyl-, $(C_6-C_{14})$-aryl which is unsubstituted or substituted by a residue $(C_1-C_2)$-alkyl, $(C_1-C_2)$-alkoxy, fluoro, or chloro; heteroaryl-, $(C_6-C_{14})$-aryl-$(C_1-C_4)$-alkyl- where aryl is unsubstituted or substituted by a residue $(C_1-C_2)$-alkyl, $(C_1-C_2)$-alkoxy, fluoro, or chloro; or heteroaryl-$(C_1-C_4)$-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemihydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound'.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen. group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a chemical entity which has biological activity. In some embodiments, an "active agent" is a compound having pharmaceutical utility. For example an active agent may be an anti-neurodegenerative therapeutic.

The term "therapeutically effective amount" of a chemical entity described herein means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of KMO activity. In some embodiments, a therapeutically effective amount is an amount sufficient to treat the symptoms of neurodegenerative pathway or disease, such as Huntington's disease, Alzheimer's disease, Parkinson's disease, olivoponto cerebellar atrophy, non-Alzheimer's dementia, multi-infarctual dementia, cerebral amyotrophic lateral sclerosis, cerebral ischemia, cerebral hypoxia, spinal or head trauma, or epilepsy. In some embodiments a therapeutically effective amount is an amount sufficient to reduce the signs or side effects of a neurodegenerative disease. In some embodiments, a therapeutically effective amount of a chemical entity is an amount sufficient to prevent a significant increase or significantly reduce the level of neuronal cell death. In some embodiments a therapeutically effective amount is an amount sufficient to reduce the signs or side effects of a neurodegenerative disease. In some embodiments, a therapeutically effective amount of a chemical entity is an amount sufficient to prevent a significant increase or significantly reduce the level of QUIN associated with neuronal cell death. In some embodiments, a therapeutically effective amount of a chemical entity is an amount sufficient to effect an increase in the level of KYNA associated with neuronal cell health. In some embodiments, a therapeutically effective amount of a chemical entity is an amount sufficient to increase the anticonvulsant and neuroprotective properties associated with lowered levels of QUIN and increased levels of KYNA.

In methods described herein for treating a neurodegenerative disorder, a therapeutically effective amount may also be an amount sufficient, when administered to a patient, to detectably slow the progression of the neurodegenative disease, or prevent the patient to whom the chemical entity is given from presenting symptoms of the neurodegenative disease. In some methods described herein for treating a neurodegenative disease, a therapeutically effective amount may also be an amount sufficient to produce a detectable decrease in the level of neuronal cell death. For example, in some embodiments a therapeutically effective amount is an amount of a chemical entity described herein sufficient to significantly decrease the level of neuronal death by effecting a detectable decrease in the amount of QUIN, and an increase in the amount of KYNA.

The term "inhibition" indicates a significant decrease in the baseline activity of a biological activity or process. "Inhibition of KMO activity" refers to a decrease in KMO activity as a direct or indirect response to the presence of at least one chemical entity described herein, relative to the activity of KMO in the absence of at least one chemical entity. The decrease in activity may be due to the direct interaction of the compound with KMO, or due to the interaction of the chemical entity(ies) described herein with one or more other factors that in turn affect KMO activity. For example, the presence of the chemical entity(ies) may decrease KMO activity by directly binding to the KMO, by causing (directly or indirectly) another factor to decrease KMO activity, or by (directly or indirectly) decreasing the amount of KMO present in the cell or organism.

"Inhibition of KMO activity" refers to a decrease in KMO activity as a direct or indirect response to the presence of at least one chemical entity described herein, relative to the activity of KMO in the absence of the at least one chemical entity. The decrease in activity may be due to the direct interaction of the compound with KMO or with one or more other factors that in turn affect KMO activity.

Inhibition of KMO activity also refers to an observable inhibition of 3-HK and QUIN production in a standard assay such as the assay described below. The inhibition of KMO activity also refers to an observable increase in the production of KYNA. In some embodiments, the chemical entity described herein has an $IC_{50}$ value less than or equal to 1 micromolar. In some embodiments, the chemical entity has an $IC_{50}$ value less than or equal to less than 100 micromolar. In some embodiments, the chemical entity has an $IC_{50}$ value less than or equal to 10 nanomolar.

"KMO activity" also includes activation, redistribution, reorganization, or capping of one or more various KMO membrane receptors, or receptor sites can undergo redistribution and capping that can initiate signal transduction. KMO activity also includes the synthesis or production of QUIN and 3-HK.

A "disease responsive to inhibition of KMO activity" is a disease in which inhibiting KMO provides a therapeutic benefit such as an amelioration of symptoms, decrease in disease progression, prevention or delay of disease onset, or inhibition of aberrant activity and/or death of certain cell-types (neuronal cells).

"Treatment" or "treating" means any treatment of a disease in a patient, including:
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Subject" or "patient' refers to an animal, such as a mammal, that has been or will be the object of treatment, observation or experiment. The methods described herein may be useful in both human therapy and veterinary applications. In some embodiments, the subject is a mammal; and in some embodiments the subject is human.

Provided is at least one chemical entity chosen from compounds of formula I

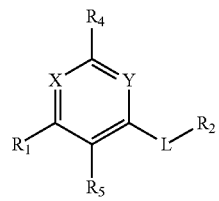

Formula I and pharmaceutically acceptable salts and prodrugs thereof wherein:

X and Y are independently chosen from CH and N provided that at least one of X and Y is N;

$R_1$ is chosen from aryl and heteroaryl, each of which is substituted with one, two, or three groups chosen from halo, optionally substituted lower alkyl, lower alkoxy, optionally substituted amino, optionally substituted heterocycloalkyl, optionally substituted heteroaryl, and hydroxy;

L is chosen from —C(O)O—, —C(O)N($R_3$)—, —N($R_3$)C(O)—, —N($R_3$)S(O)$_2$—, and —S(O)$_2$N($R_3$)—;

$R_2$ is chosen from hydrogen, optionally substituted lower alkyl, optionally substituted aryl, optionally substituted heteroaryl, optionally substituted cycloalkyl, and optionally substituted heterocycloalkyl, provided that when L is —N($R_3$)S(O)$_2$—, $R_2$ is not hydrogen;

$R_3$ is chosen from hydrogen and lower alkyl; or $R_2$ and $R_3$, taken together with any intervening atoms, forms an optionally substituted heterocycloalkyl ring;

$R_4$ is chosen from hydrogen and optionally substituted lower alkyl;

$R_5$ is chosen from hydrogen and fluoro, provided that the compound of Formula I is not
N-(1-hydroxy-3-(1H-indol-3-yl)propan-2-yl)-6-(4-methoxyphenyl)pyrimidine-4-carboxamide,
3-chloro-2-methyl-N-(6-phenylpyrimidin-4-yl)benzenesulfonamide;
4-methoxy-N-(6-phenylpyrimidin-4-yl)benzamide;
N-(6-phenylpyrimidin-4-yl)benzamide;
6-phenylpyrimidine-4-carboxylic acid;
methyl 6-phenylpyrimidine-4-carboxylate;

ethyl 6-phenylpyrimidine-4-carboxylate;
6-phenylpyrimidine-4-carboxamide;
N-methyl-6-phenylpyrimidine-4-carboxamide; or
N,N-dimethyl-6-phenylpyrimidine-4-carboxamide.

In some embodiments, the compound of Formula I is chosen from compounds of Formula II

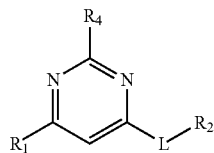

Formula II wherein:
$R_1$ is chosen from aryl and heteroaryl, each of which is substituted with one, two, or three groups chosen from halo, lower alkyl, lower alkoxy, optionally substituted amino, optionally substituted heterocycloalkyl, optionally substituted heteroaryl, and hydroxy;
L is chosen from —C(O)O—, —C(O)N($R_3$)—, —N($R_3$)C(O)—, —N($R_3$)S(O)$_2$—, and —S(O)$_2$N($R_3$)—;
$R_2$ is chosen from hydrogen, optionally substituted lower alkyl, optionally substituted aryl, optionally substituted heteroaryl, optionally substituted cycloalkyl, and optionally substituted heterocycloalkyl, provided that when L is —N($R_3$)S(O)$_2$—, $R_2$ is not hydrogen;
$R_3$ is chosen from hydrogen and lower alkyl; and
$R_4$ is chosen from hydrogen and optionally substituted lower alkyl;
provided that the compound of Formula II is not
N-(1-hydroxy-3-(1H-indol-3-yl)propan-2-yl)-6-(4-methoxyphenyl)pyrimidine-4-carboxamide,
3-chloro-2-methyl-N-(6-phenylpyrimidin-4-yl)benzenesulfonamide;
4-methoxy-N-(6-phenylpyrimidin-4-yl)benzamide;
N-(6-phenylpyrimidin-4-yl)benzamide;
6-phenylpyrimidine-4-carboxylic acid;
methyl 6-phenylpyrimidine-4-carboxylate;
ethyl 6-phenylpyrimidine-4-carboxylate;
6-phenylpyrimidine-4-carboxamide;
N-methyl-6-phenylpyrimidine-4-carboxamide; or
N,N-dimethyl-6-phenylpyrimidine-4-carboxamide.

In some embodiments, $R_1$ is phenyl optionally substituted with one, two, or three groups chosen from halo, lower alkyl, lower alkoxy, optionally substituted amino, optionally substituted heterocycloalkyl, optionally substituted heteroaryl, and hydroxy. In some embodiments, $R_1$ is phenyl optionally substituted with one, two, or three groups chosen from halo, optionally substituted lower alkyl, optionally substituted lower alkoxy, and hydroxy. In some embodiments, $R_1$ is phenyl optionally substituted with one, two, or three groups chosen from halo, lower alkyl, trifluoromethyl, lower alkoxy, and hydroxy. In some embodiments, $R_1$ is phenyl optionally substituted with one, two, or three groups chosen from halo, lower alkyl, and trifluoromethyl. In some embodiments, $R_1$ is chosen from phenyl, 2,4-difluorophenyl, 3-chloro-2-fluorophenyl, 3-chloro-4-trifluoromethylphenyl, 2-fluoro-5-trifluoromethylphenyl, 3-fluoro-5-trifluoromethylphenyl, 3-trifluoromethylphenyl, 4-fluoro-3-trifluoromethylphenyl, 2-trifluoromethylphenyl, 3,4-dichlorophenyl, 3-chlorophenyl, 4-chlorophenyl, and 3,5-dichlorophenyl. In some embodiments, $R_1$ is chosen from 2-trifluoromethylphenyl, 3,4-dichlorophenyl, 3-chlorophenyl, 4-chlorophenyl, and 3,5-dichlorophenyl.

In some embodiments, $R_1$ is pyridin-3-yl optionally substituted with one, two, or three groups chosen from halo, lower alkyl, lower alkoxy, optionally substituted amino, optionally substituted heterocycloalkyl, optionally substituted heteroaryl, and hydroxy. In some embodiments, $R_1$ is pyridin-3-yl optionally substituted with one, two, or three groups chosen from halo, optionally substituted lower alkyl, optionally substituted lower alkoxy, and hydroxy. In some embodiments, $R_1$ is pyridin-3-yl optionally substituted with one, two, or three groups chosen from halo, lower alkyl, trifluoromethyl, lower alkoxy, and hydroxy. In some embodiments, $R_1$ is pyridin-3-yl optionally substituted with one, two, or three groups chosen from halo, lower alkyl, and trifluoromethyl. In some embodiments, $R_1$ is chosen from pyridin-3-yl, 5-fluoropyridin-3-yl, and 5-chloropyridin-3-yl.

In some embodiments, L is chosen from —C(O)O—, —C(O)N($R_3$)—, and —N($R_3$)S(O)$_2$—. In some embodiments, L is —C(O)N($R_3$)—. In some embodiments, L is —N($R_3$)S(O)$_2$—. In some embodiments, L is —C(O)O—.

In some embodiments, $R_3$ is hydrogen. In some embodiments, $R_3$ is lower alkyl. In some embodiments, $R_3$ is methyl.

In some embodiments, $R_4$ is chosen from hydrogen and lower alkyl. In some embodiments, $R_4$ is hydrogen. In some embodiments, $R_4$ is lower alkyl. In some embodiments, $R_4$ is methyl.

In some embodiments, $R_2$ is chosen from hydrogen, lower alkyl, optionally substituted heteroaryl, and optionally substituted phenyl. In some embodiments, $R_2$ is chosen from hydrogen, lower alkyl, optionally substituted pyridinyl, and optionally substituted phenyl. In some embodiments, $R_2$ is chosen from hydrogen, lower alkyl, pyridinyl, and phenyl, wherein the pyridinyl and phenyl groups are each optionally substituted with one or two groups chosen from halo, hydroxy, lower alkyl, and lower alkoxy. In some embodiments, $R_2$ is chosen from hydrogen, lower alkyl, pyridinyl, and phenyl, wherein the phenyl group is optionally substituted with one or two groups chosen from halo, hydroxy, lower alkyl, and lower alkoxy.

In some embodiments, $R_2$ and $R_3$, taken together with any intervening atoms, forms an optionally substituted heterocycloalkyl ring. In some embodiments, $R_2$ and $R_3$, taken together with any intervening atoms, forms an optionally substituted heterocycloalkyl ring chosen from morpholin-4-yl, 3,4-dihydroquinolin-1(2H)-yl, indolin-1-yl, 3-oxopiperazin-1-yl, piperidin-1-yl, piperazin-1-yl, pyrrolidin-1-yl, azetidin-1-yl, and isoindolin-2-yl, each of which is optionally substituted. In some embodiments, $R_2$ and $R_3$, taken together with any intervening atoms, forms an optionally substituted heterocycloalkyl ring chosen from morpholin-4-yl, 3,4-dihydroquinolin-1(2H)-yl, indolin-1-yl, 3-oxopiperazin-1-yl, piperidin-1-yl, piperazin-1-yl, pyrrolidin-1-yl, azetidin-1-yl, and isoindolin-2-yl, each of which is optionally substituted with one or two groups chosen from halo, hydroxy, lower alkyl, lower alkoxy, —C(O)(lower alkyl), —C(O)NH$_2$, —C(O)N(H)(lower alkyl), and —C(O)(lower alkyl)(lower alkyl).

In some embodiments, $R_5$ is hydrogen. In some embodiments, $R_5$ is fluoro.

In some embodiments, X is N and Y is CH.
In some embodiments, X is CH and Y is N.
In some embodiments, X is N and Y is N.

Also provided is at least one chemical entity chosen from
6-(2-Trifluoromethyl-phenyl)-pyrimidine-4-carboxylic acid;
N-[6-(2-Trifluoromethyl-phenyl)-pyrimidin-4-yl]-methanesulfonamide;
3,4-Dimethoxy-N-[6-(2-trifluoromethyl-phenyl)-pyrimidin-4-yl]-benzenesulfonamide;

N-[6-(3,4-Dichloro-phenyl)-pyrimidin-4-yl]-methanesulfonamide;
6-(3,4-Dichloro-phenyl)-pyrimidine-4-carboxylic acid methyl ester;
N-[6-(3,4-Dichloro-phenyl)-pyrimidin-4-yl]-3,4-dimethoxy-benzenesulfonamide;
6-(3-Chloro-phenyl)-pyrimidine-4-carboxylic acid methyl ester;
6-(3-Chloro-phenyl)-pyrimidine-4-carboxylic acid;
6-(3,4-Dichloro-phenyl)-pyrimidine-4-carboxylic acid pyridin-3-ylamide;
6-(3-Chloro-phenyl)-pyrimidine-4-carboxylic acid pyridin-3-ylamide;
6-(3,4-Dichloro-phenyl)-pyrimidine-4-carboxylic acid;
6-(3,5-Dichloro-phenyl)-pyrimidine-4-carboxylic acid;
6-(3,5-Dichloro-phenyl)-pyrimidine-4-carboxylic acid methyl ester;
N-[6-(3-Chloro-phenyl)-pyrimidin-4-yl]-nicotinamide;
6-(3,4-Dichloro-phenyl)-2-methyl-pyrimidine-4-carboxylic acid methyl ester;
6-(3,4-Dichloro-phenyl)-2-methyl-pyrimidine-4-carboxylic acid;
6-(3,4-Dichloro-phenyl)-2-methyl-pyrimidine-4-carboxylic acid pyridin-3-ylamide;
6-(3-Chloro-phenyl)-pyrimidine-4-carboxylic acid (2,6-dimethyl-pyridin-3-yl)-amide;
6-(3-Chloro-phenyl)-pyrimidine-4-carboxylic acid pyrimidin-5-ylamide;
6-(4-Morpholin-4-yl-phenyl)-pyrimidine-4-carboxylic acid methyl ester;
6-(4-Fluoro-3-trifluoromethyl-phenyl)-pyrimidine-4-carboxylic acid methyl ester;
6-(3-Trifluoromethyl-phenyl)-pyrimidine-4-carboxylic acid methyl ester;
6-(4-Fluoro-3-trifluoromethyl-phenyl)-pyrimidine-4-carboxylic acid;
6-(3-Trifluoromethyl-phenyl)-pyrimidine-4-carboxylic acid pyridin-2-ylamide;
6-(4-Fluoro-3-trifluoromethyl-phenyl)-pyrimidine-4-carboxylic acid pyridin-3-ylamide;
6-(3,5-Dichloro-phenyl)-pyrimidine-4-carboxylic acid pyridin-3-ylamide;
6-(3-Trifluoromethyl-phenyl)-pyrimidine-4-carboxylic acid pyridin-3-ylamide;
6-(3-Trifluoromethyl-phenyl)-pyrimidine-4-carboxylic acid;
6-(3-Chloro-phenyl)-pyrimidine-4-carboxylic acid ethylamide;
6-(5-Fluoro-pyridin-3-yl)-pyrimidine-4-carboxylic acid;
6-(3-Chloro-phenyl)-pyrimidine-4-carboxylic acid amide;
6-(3-Fluoro-5-trifluoromethyl-phenyl)-pyrimidine-4-carboxylic acid methyl ester;
6-(3-Chloro-phenyl)-pyrimidine-4-carboxylic acid methylamide;
6-(5-Fluoro-pyridin-3-yl)-pyrimidine-4-carboxylic acid methyl ester;
6-(3-Fluoro-5-trifluoromethyl-phenyl)-pyrimidine-4-carboxylic acid;
6-(5-Chloro-pyridin-3-yl)-pyrimidine-4-carboxylic acid methyl ester;
6-(5-Chloro-pyridin-3-yl)-pyrimidine-4-carboxylic acid;
6-(2-Fluoro-5-trifluoromethyl-phenyl)-pyrimidine-4-carboxylic acid methyl ester;
6-(3-Chloro-phenyl)-pyrimidine-4-carboxylic acid isopropylamide;
[6-(3-Chloro-phenyl)-pyrimidin-4-yl]-morpholin-4-yl-methanone;
6-(3-Chloro-phenyl)-pyrimidine-4-carboxylic acid propylamide;
6-(3-Chloro-phenyl)-pyrimidine-4-carboxylic acid phenylamide;
6-Phenyl-pyrimidine-4-carboxylic acid;
6-(2-Fluoro-5-trifluoromethyl-phenyl)-pyrimidine-4-carboxylic acid;
6-(3-Chloro-phenyl)-pyrimidine-4-carboxylic acid o-tolylamide;
6-(3-Chloro-phenyl)-pyrimidine-4-carboxylic acid p-tolylamide;
[6-(3-Chloro-phenyl)-pyrimidin-4-yl]-(3,4-dihydro-2H-quinolin-1-yl)-methanone;
6-Phenyl-pyrimidine-4-carboxylic acid methyl ester;
6-(2,4-Difluoro-phenyl)-pyrimidine-4-carboxylic acid methyl ester;
6-(2,4-Difluoro-phenyl)-pyrimidine-4-carboxylic acid;
6-(3-Chloro-phenyl)-pyrimidine-4-carboxylic acid (6-methoxy-pyridin-3-yl)-amide;
[6-(3-Chloro-phenyl)-pyrimidin-4-yl]-(2,3-dihydro-indol-1-yl)-methanone;
6-(3-Chloro-phenyl)-pyrimidine-4-carboxylic acid m-tolylamide;
6-(3-Chloro-phenyl)-pyrimidine-4-carboxylic acid methyl-pyridin-3-yl-amide;
6-(3-Chloro-phenyl)-pyrimidine-4-carboxylic acid (5-methoxy-pyridin-3-yl)-amide;
6-(3-Chloro-2-fluoro-phenyl)-pyrimidine-4-carboxylic acid methyl ester;
6-(3-Chloro-phenyl)-pyrimidine-4-carboxylic acid dimethylamide;
6-(3-Chloro-phenyl)-2-methyl-pyrimidine-4-carboxylic acid methyl ester;
4-[6-(3-Chloro-phenyl)-pyrimidine-4-carbonyl]-piperazin-2-one;
6-Phenyl-pyrimidine-4-carboxylic acid pyridin-3-ylamide;
6-(3-Chloro-2-fluoro-phenyl)-pyrimidine-4-carboxylic acid;
6-(3,4-Dichloro-phenylamino)-pyrimidine-4-carboxylic acid methyl ester;
6-(3-Chloro-phenyl)-pyrimidine-4-carboxylic acid (4-methoxy-pyridin-3-yl)-amide;
6-(3-Chloro-phenyl)-2-methyl-pyrimidine-4-carboxylic acid;
6-(3-Chloro-phenyl)-2-methyl-pyrimidine-4-carboxylic acid pyridin-3-ylamide;
6-(3-Chloro-phenyl)-pyrimidine-4-carboxylic acid (2-hydroxy-ethyl)-amide;
[6-(3-Chloro-phenyl)-pyrimidin-4-yl]-(4-hydroxy-piperidin-1-yl)-methanone;
6-(3-Methoxy-phenyl)-pyrimidine-4-carboxylic acid;
6-(3-Methoxy-phenyl)-pyrimidine-4-carboxylic acid methyl ester;
6-(3-Chloro-phenyl)-pyrimidine-4-carboxylic acid benzylamide;
[6-(3-Chloro-phenyl)-pyrimidin-4-yl]-(4-methyl-piperazin-1-yl)-methanone;
[6-(3-Chloro-phenyl)-pyrimidin-4-yl]-pyrrolidin-1-yl-methanone;
6-(3-Chloro-phenyl)-pyrimidine-4-carboxylic acid ((S)-2-hydroxy-propyl)-amide;
6-m-Tolyl-pyrimidine-4-carboxylic acid methyl ester;
1-{-4-[6(3-Chloro-phenyl)-pyrimidine-4-carbonyl]-piperazin-1-yl}-ethanone;
6-(3-Chloro-phenyl)-pyrimidine-4-carboxylic acid ((R)-2-hydroxy-propyl)-amide;
6-(3-Chloro-phenyl)-pyrimidine-4-carboxylic acid (2-methoxy-phenyl)-amide;

6-(3-Chloro-phenyl)-pyrimidine-4-carboxylic acid (4-methoxy-phenyl)-amide;
6-(3-Chloro-phenyl)-pyrimidine-4-carboxylic acid (3-methoxy-phenyl)-amide; Sodium; 6-(3-chloro-phenyl)-pyrimidine-4-sulfonate;
6-m-Tolyl-pyrimidine-4-carboxylic acid;
6-(3-Chloro-phenyl)-pyrimidine-4-carboxylic acid methyl-phenyl-amide;
[6-(3,4-Dichloro-phenyl)-pyrimidin-4-yl]-(2,3-dihydro-indol-1-yl)-methanone;
N-[6-(3-Chloro-phenyl)-pyrimidine-4-carbonyl]-methanesulfonamide;
6-(3-Chloro-phenyl)-pyrimidine-4-carboxylic acid pyridin-2-ylamide;
6-(3-Chloro-phenyl)-pyrimidine-4-carboxylic acid pyridin-4-ylamide;
6-(3-Chloro-phenyl)-pyrimidine-4-carboxylic acid (pyridin-4-ylmethyl)-amide;
[6-(3-Chloro-phenyl)-pyrimidin-4-yl]-(4-methyl-piperidin-1-yl)-methanone;
[6-(3-Chloro-phenyl)-pyrimidin-4-yl]-((R)-3-hydroxy-pyrrolidin-1-yl)-methanone;
6-(3-Chloro-phenyl)-pyrimidine-4-carboxylic acid [1,3,4]thiadiazol-2-ylamide;
6-(3-Chloro-phenyl)-pyrimidine-4-carboxylic acid isoxazol-3-ylamide;
6-(3-Chloro-phenyl)-pyrimidine-4-carboxylic acid ((R)-1-phenyl-ethyl)-amide;
6-(3-Chloro-phenyl)-pyrimidine-4-carboxylic acid ((S)-1-phenyl-ethyl)-amide;
[6-(3-Chloro-phenyl)-pyrimidin-4-yl]-((S)-3-hydroxy-pyrrolidin-1-yl)-methanone;
6-(3-Chloro-phenyl)-pyrimidine-4-carboxylic acid[4-(4-methyl-piperazin-1-yl)-phenyl]-amide;
6-(3-Chloro-phenyl)-pyrimidine-4-carboxylic acid (6-trifluoromethyl-pyridin-3-yl)-amide;
6-(3-Chloro-phenyl)-pyrimidine-4-carboxylic acid (pyridin-3-ylmethyl)-amide;
6-(3-Chloro-phenyl)-pyrimidine-4-carboxylic acid pyridazin-3-ylamide;
6-(3-Chloro-phenyl)-pyrimidine-4-carboxylic acid pyrazin-2-ylamide;
6-(3-Chloro-phenyl)-pyrimidine-4-carboxylic acid (4-morpholin-4-yl-phenyl)-amide;
(S)-1-[6-(3-Chloro-phenyl)-pyrimidine-4-carbonyl]-pyrrolidine-2-carboxylic acid amide;
(R)-1-[6-(3-Chloro-phenyl)-pyrimidine-4-carbonyl]-pyrrolidine-2-carboxylic acid amide;
Azetidin-1-yl-[6-(3-chloro-phenyl)-pyrimidin-4-yl]-methanone;
6-(4-Methoxy-phenyl)-pyrimidine-4-carboxylic acid;
[6-(3-Chloro-phenyl)-pyrimidin-4-yl]-(1,3-dihydro-isoindol-2-yl)-methanone;
[6-(3,4-Dichloro-phenyl)-pyrimidin-4-yl]-(3,4-dihydro-2H-quinolin-1-yl)-methanone;
6-(3,4-Dichloro-phenyl)-pyrimidine-4-carboxylic acid phenylamide;
6-(3,4-Dichloro-phenyl)-pyrimidine-4-carboxylic acid p-tolylamide;
6-(3,4-Dichloro-phenyl)-pyrimidine-4-carboxylic acid (5-methoxy-pyridin-3-yl)-amide;
6-(3,4-Dichloro-phenyl)-pyrimidine-4-carboxylic acid pyrimidin-5-ylamide;
6-(3,4-Dichloro-phenyl)-pyrimidine-4-carboxylic acid (6-methyl-pyridin-3-yl)-amide;
6-(3,4-Dichloro-phenyl)-pyrimidine-4-carboxylic acid (2-methyl-pyridin-3-yl)-amide;
6-(3-Chloro-phenyl)-pyrimidine-4-carboxylic acid pyrimidin-2-ylamide;
6-(3-Chloro-phenyl)-pyrimidine-4-carboxylic acid methyl-p-tolyl-amide;
6-(3-Fluoro-phenyl)-pyrimidine-4-carboxylic acid methyl ester;
6-(3-Chloro-phenyl)-pyrimidine-4-carboxylic acid (6-methyl-pyridin-3-yl)-amide;
6-(3-Chloro-phenyl)-pyrimidine-4-carboxylic acid (2-methyl-pyridin-3-yl)-amide;
6-(3-Chloro-phenyl)-pyrimidine-4-carboxylic acid (4-fluoro-phenyl)-amide;
6-(3-Fluoro-phenyl)-pyrimidine-4-carboxylic acid;
6-(3,5-Dichloro-phenyl)-pyrimidine-4-carboxylic acid phenylamide;
[6-(3,5-Dichloro-phenyl)-pyrimidin-4-yl]-(2,3-dihydro-indol-1-yl)-methanone;
6-(3,5-Dichloro-phenyl)-pyrimidine-4-carboxylic acid p-tolylamide;
6-(3,5-Dichloro-phenyl)-pyrimidine-4-carboxylic acid (5-methoxy-pyridin-3-yl)-amide;
6-(3-Chloro-phenyl)-pyrimidine-4-carboxylic acid (1-methyl-1H-pyrazol-3-yl)-amide;
6-(3-Chloro-phenyl)-pyrimidine-4-carboxylic acid (1-methyl-1H-pyrazol-4-yl)-amide;
6-(3-Chloro-phenyl)-pyrimidine-4-carboxylic acid (4-methoxy-phenyl)-methyl-amide;
[6-(3-Chloro-phenyl)-pyrimidin-4-yl]-(2-methyl-2,3-dihydro-indol-1-yl)-methanone;
6-(3-Fluoro-phenyl)-pyrimidine-4-carboxylic acid pyridin-3-ylamide;
6-(3-Chloro-phenyl)-pyrimidine-4-carboxylic acid (2,2-difluoro-benzo[1,3]dioxol-5-yl)-amide;
[6-(3-Chloro-phenyl)-pyrimidin-4-yl]-(5-fluoro-2,3-dihydro-indol-1-yl)-methanone;
(5-Chloro-2,3-dihydro-indol-1-yl)-[6-(3-chloro-phenyl)-pyrimidin-4-yl]-methanone;
6-(3,5-Dichloro-phenyl)-pyrimidine-4-carboxylic acid pyrimidin-5-ylamide;
6-(3-Chloro-4-trifluoromethyl-phenyl)-pyrimidine-4-carboxylic acid methyl ester;
6-(3-Chloro-4-trifluoromethyl-phenyl)-pyrimidine-4-carboxylic acid;
6-(3-Chloro-4-trifluoromethyl-phenyl)-pyrimidine-4-carboxylic acid pyridin-3-ylamide;
[6-(3-Chloro-phenyl)-pyrimidin-4-yl]-(2,3-dihydro-pyrrolo[3,2-c]pyridin-1-yl)-methanone;
6-(3-Chloro-phenyl)-pyrimidine-4-carboxylic acid (2,2-difluoro-benzo[1,3]dioxol-5-yl)-methyl-amide;
6-(3-Chloro-phenyl)-pyrimidine-4-carboxylic acid thiazol-2-ylamide;
6-(3-Chloro-phenyl)-pyrimidine-4-carboxylic acid (3-methyl-isoxazol-5-yl)-amide;
6-(3-Chloro-phenyl)-pyrimidine-4-carboxylic acid (5-methyl-[1,3,4]oxadiazol-2-yl)-amide;
6-(3-Chloro-phenyl)-pyrimidine-4-carboxylic acid oxazol-2-ylamide;
6-(3-Chloro-phenyl)-pyrimidine-4-carboxylic acid (3-methyl-[1,2,4]thiadiazol-5-yl)-amide;
6-(3-Chloro-phenyl)-pyrimidine-4-carboxylic acid (4H-[1,2,4]triazol-3-yl)-amide;
6-(3,4-Difluoro-phenyl)-pyrimidine-4-carboxylic acid methyl ester;
6-(5-Chloro-2-fluoro-phenyl)-pyrimidine-4-carboxylic acid methyl ester;
6-(3,4-Difluoro-phenyl)-pyrimidine-4-carboxylic acid;

6-(3,4-Difluoro-phenyl)-pyrimidine-4-carboxylic acid pyrimidin-5-ylamide;
6-(5-Chloro-2-fluoro-phenyl)-pyrimidine-4-carboxylic acid;
[6-(3,4-Dichloro-phenyl)-pyrimidin-4-yl]-(1',2'-dihydro-spiro[cyclopropane-1,3'-[3H]indol]-1')-methanone;
6-(3,4-Dichloro-phenyl)-pyrimidine-4-carboxylic acid (2,6-dimethyl-pyridin-3-yl)-amide;
6-(3,4-Dichloro-phenyl)-pyrimidine-4-carboxylic acid (3-methyl-isoxazol-5-yl)-amide;
6-(3-Chloro-4-fluoro-phenyl)-pyrimidine-4-carboxylic acid methyl ester;
6-(3,4-Dichloro-phenyl)-pyrimidine-4-carboxylic acid (5-methyl-[1,3,4]oxadiazol-2-yl)-amide;
6-(3-Chloro-4-methoxy-phenyl)-pyrimidine-4-carboxylic acid methyl ester;
6-(3-Chloro-4-methoxy-phenyl)-pyrimidine-4-carboxylic acid;
6-(3,4-Dichloro-phenyl)-pyrimidine-4-carboxylic acid (pyridin-4-ylmethyl)-amide;
6-(3-Chloro-4-fluoro-phenyl)-pyrimidine-4-carboxylic acid;
6-(3,4-Dichloro-phenyl)-pyrimidine-4-carboxylic acid [1,3,4]thiadiazol-2-ylamide;
6-(3,4-Dichloro-phenyl)-pyrimidine-4-carboxylic acid (2-amino-ethyl)-amide;
(5-Chloro-2,3-dihydro-indol-1-yl)-[6-(3,4-dichloro-phenyl)-pyrimidin-4-yl]-methanone;
[6-(3,4-Dichloro-phenyl)-pyrimidin-4-yl]-(5-fluoro-2,3-dihydro-indol-1-yl)-methanone;
[6-(3,4-Dichloro-phenyl)-pyrimidin-4-yl]-(5-morpholin-4-yl-2,3-dihydro-indol-1-yl)-methanone;
6-(3,4-Dichloro-phenyl)-5-fluoro-pyrimidine-4-carboxylic acid;
6-(3,4-Dichloro-phenyl)-pyrimidine-4-carboxylic acid pyridin-4-ylamide;
6-(3,4-Dichloro-phenyl)-pyrimidine-4-carboxylic acid pyridin-2-ylamide;
6-(3,4-Dichloro-phenyl)-pyrimidine-4-carboxylic acid (1-methyl-1H-pyrazol-4-yl)-amide;
6-(3,4-Dichloro-phenyl)-pyrimidine-4-carboxylic acid isoxazol-3-ylamide;
6-(3,4-Dichloro-phenyl)-pyrimidine-4-carboxylic acid thiazol-2-ylamide;
[6-(3,4-Dichloro-phenyl)-pyrimidin-4-yl]-(1,3-dihydro-isoindol-2-yl)-methanone;
6-(3,4-Dichloro-phenyl)-pyrimidine-4-carboxylic acid (4H-[1,2,4]triazol-3-yl)-amide;
4-(3,4-Dichloro-phenyl)-6-(5-fluoro-pyridin-2-yl)-pyrimidine;
6-(3,4-Difluoro-phenyl)-pyrimidine-4-carboxylic acid pyridin-3-ylamide;
6-(3-Trifluoromethyl-phenyl)-pyrimidine-4-carboxylic acid pyrimidin-5-ylamide;
6-(3,4-Dichloro-phenyl)-pyrimidine-4-carboxylic acid (2-methyl-pyrimidin-5-yl)-amide;
6-(3-Chloro-4-methyl-phenyl)-pyrimidine-4-carboxylic acid methyl ester;
6-(3-Chloro-4-methyl-phenyl)-pyrimidine-4-carboxylic acid;
6-(3-Chloro-4-fluoro-phenyl)-pyrimidine-4-carboxylic acid pyridin-3-ylamide;
6-(3-Chloro-4-fluoro-phenyl)-pyrimidine-4-carboxylic acid (2,6-dimethyl-pyridin-3-yl)-amide;
6-(3,4-Dichloro-phenyl)-pyrimidine-4-carboxylic acid (2-acetylamino-ethyl)-amide;
[6-(3,4-Dichloro-phenyl)-pyrimidin-4-yl]-(3,3-dimethyl-2,3-dihydro-indol-1-yl)-methanone;
[6-(3,4-Dichloro-phenyl)-pyrimidin-4-yl]-(4-hydroxy-piperidin-1-yl)-methanone;
[6-(3,4-Dichloro-phenyl)-pyrimidin-4-yl]-morpholin-4-yl-methanone;
6-(3-Chloro-4-fluoro-phenyl)-pyrimidine-4-carboxylic acid pyrimidin-5-ylamide;
6-(3,4-Dichloro-phenyl)-5-fluoro-pyrimidine-4-carboxylic acid methyl ester;
6-(3,4-Dichloro-phenyl)-5-fluoro-pyrimidine-4-carboxylic acid;
6-(3,4-Dichloro-phenyl)-5-fluoro-pyrimidine-4-carboxylic acid pyridin-3-ylamide;
6-(3,4-Dichloro-phenyl)-5-fluoro-pyrimidine-4-carboxylic acid (2,6-dimethyl-pyridin-3-yl)-amide;
6-(3,4-Dichloro-phenyl)-5-fluoro-pyrimidine-4-carboxylic acid pyrimidin-5-ylamide;
2-(3-Chloro-phenyl)-isonicotinic acid methyl ester;
4-(3-Chloro-phenyl)-pyridine-2-carboxylic acid;
4-(3-Chloro-phenyl)-pyridine-2-carboxylic acid methyl ester;
4-(3-Chloro-phenyl)-pyridine-2-carboxylic acid pyridin-3-ylamide;
4-(3-Chloro-phenyl)-pyridine-2-carboxylic acid phenylamide;
[4-(3-Chloro-phenyl)-pyridin-2-yl]-(2,3-dihydro-indol-1-yl)-methanone;
4-(3-Chloro-phenyl)-pyridine-2-carboxylic acid p-tolylamide;
4-(3-Chloro-phenyl)-pyridine-2-carboxylic acid (5-methoxy-pyridin-3-yl)-amide;
4-(3,5-Dichloro-phenyl)-pyridine-2-carboxylic acid phenylamide;
4-(3,5-Dichloro-phenyl)-pyridine-2-carboxylic acid p-tolylamide;
4-(3,5-Dichloro-phenyl)-pyridine-2-carboxylic acid pyridin-3-ylamide;
4-(3,5-Dichloro-phenyl)-pyridine-2-carboxylic acid (5-methoxy-pyridin-3-yl)-amide;
[4-(3,5-Dichloro-phenyl)-pyridin-2-yl]-(2,3-dihydro-indol-1-yl)-methanone;
4-(3-Chloro-phenyl)-pyridine-2-carboxylic acid pyrimidin-5-ylamide;
4-(3,4-Dichloro-phenyl)-pyridine-2-carboxylic acid phenylamide;
4-(3,4-Dichloro-phenyl)-pyridine-2-carboxylic acid p-tolylamide;
4-(3,4-Dichloro-phenyl)-pyridine-2-carboxylic acid pyridin-3-ylamide;
[4-(3,4-Dichloro-phenyl)-pyridin-2-yl]-(2,3-dihydro-indol-1-yl)-methanone;
4-(3,4-Dichloro-phenyl)-pyridine-2-carboxylic acid (5-methoxy-pyridin-3-yl)-amide;
4-(3,4-Dichloro-phenyl)-pyridine-2-carboxylic acid pyrimidin-5-ylamide;
4-(3,5-Dichloro-phenyl)-pyridine-2-carboxylic acid pyrimidin-5-ylamide; and
5-Morpholin-4-yl-pyridine-2-carboxylic acid tert-butyl ester, and pharmaceutically acceptable salts and prodrugs thereof.
Also provided is at least one chemical entity chosen from
6-(3-chloro-phenyl)-pyrimidine-4-carboxylic acid sodium salt;
6-(3-Chloro-phenyl)-pyrimidine-4-carboxylic acid cyclohexyl ammonium salt;
6-(3-Chloro-phenyl)-pyrimidine-4-carboxylic acid pyridin-3-ylamide hydrochloride salt;

6-(3,4-dichloro-phenyl)-pyrimidine-4-carboxylic acid sodium salt;
6-Pyridin-3-yl-pyrimidine-4-carboxylic acid methyl ester trifluoroacetic acid salt;
6-Morpholin-4-yl-pyrimidine-4-carboxylic acid hydrochloride salt;
6-(3,4-Dichloro-phenyl)-pyrimidine-4-carboxylic acid (6-methyl-pyridin-3-yl)-amide hydrochloride salt;
6-(3,4-Dichloro-phenyl)-pyrimidine-4-carboxylic acid (2,6-dimethyl-pyridin-3-yl)-amide hydrochloride salt;
6-(3,4-Dichloro-phenyl)-pyrimidine-4-sulfonate sodium salt;
2-(3-Chloro-phenyl)-isonicotinic acid hydrochloride salt;
4-(3,5-Dichloro-phenyl)-pyridine-2-carboxylic acid hydrocloride salt; and
4-(3,4-Dichloro-phenyl)-pyridine-2-carboxylic acid hydrochloride salt.

Also provided is at least one chemical entity chosen from
6-(2-Trifluoromethyl-phenyl)-pyrimidine-4-carboxylic acid methyl ester;
6-(3,4-Dichloro-phenyl)-pyrimidine-4-carboxylic acid methyl ester;
6-(3-Chloro-phenyl)-pyrimidine-4-carboxylic acid methyl ester;
6-(3,5-Dichloro-phenyl)-pyrimidine-4-carboxylic acid methyl ester;
6-(3,4-Dichloro-phenyl)-2-methyl-pyrimidine-4-carboxylic acid methyl ester;
6-(2-Trifluoromethyl-phenyl)-pyrimidine-4-carboxylic acid;
6-(3,4-Dichloro-phenyl)-pyrimidine-4-carboxylic acid;
6-(3-Chloro-phenyl)-pyrimidine-4-carboxylic acid;
6-(3,5-Dichloro-phenyl)-pyrimidine-4-carboxylic acid;
6-(3,4-Dichloro-phenyl)-2-methyl-pyrimidine-4-carboxylic acid;
6-(3,4-Dichloro-phenyl)-pyrimidine-4-carboxylic acid pyridin-3-ylamide;
6-(3-Chloro-phenyl)-pyrimidine-4-carboxylic acid pyridin-3-ylamide;
6-(3-Chloro-phenyl)-pyrimidine-4-carboxylic acid (2,6-dimethyl-pyridin-3-yl)-amide;
6-(3,4-Dichloro-phenyl)-2-methyl-pyrimidine-4-carboxylic acid pyridin-3-ylamide;
N-[6-(3-Chloro-phenyl)-pyrimidin-4-yl]-nicotinamide;
N-[6-(3,4-Dichloro-phenyl)-pyrimidin-4-yl]-3,4-dimethoxy-benzenesulfonamide;
3,4-Dimethoxy-N-[6-(2-trifluoromethyl-phenyl)-pyrimidin-4-yl]-benzenesulfonamide;
N-[6-(3,4-Dichloro-phenyl)-pyrimidin-4-yl]-methanesulfonamide; and
N-[6-(2-Trifluoromethyl-phenyl)-pyrimidin-4-yl]-methanesulfonamide;
and pharmaceutically acceptable salts and prodrugs thereof.

Also provided is a method of treating a condition or disorder mediated by Kynurenine 3-mono-oxygenase activity in a subject in need of such a treatment which method comprises administering to the subject a therapeutically effective amount of at least one chemical entity described herein.

Methods for obtaining the chemical entities described herein will be apparent to those of ordinary skill in the art, suitable procedures being described, for example, in the reaction schemes and examples below, and in the references cited herein.

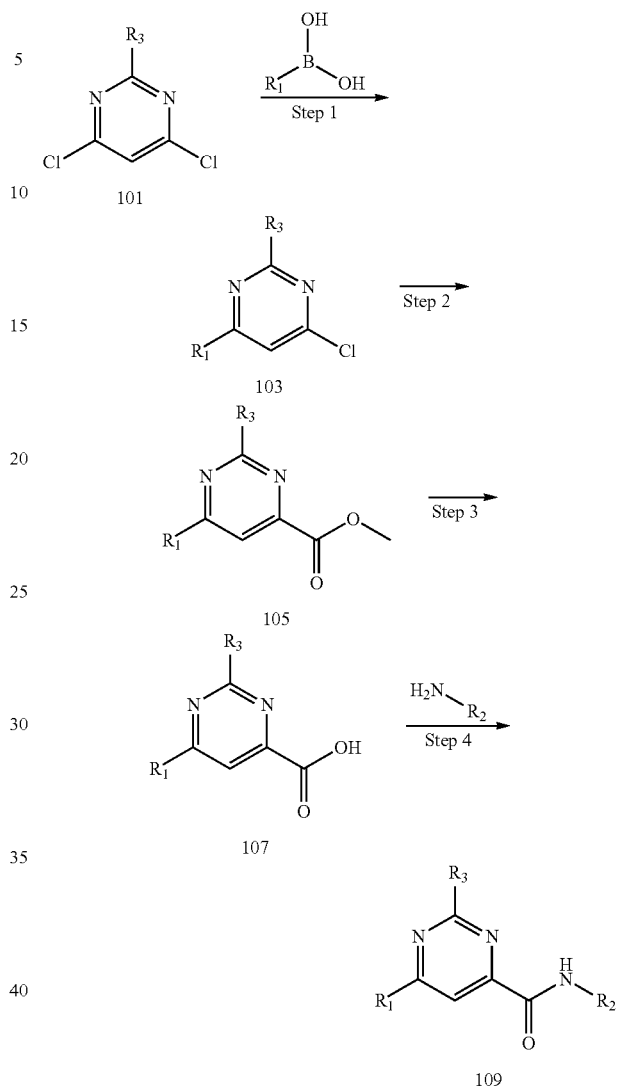

Reaction Scheme 1

Referring to Reaction Scheme 1, Step 1, a compound of formula 101, a compound of formula $R_1B(OH)_2$ and $Pd(PPh_3)_4$ are suspended in a suitable solvent such as dioxane in a pressure tube. A base such as aqueous potassium carbonate, for example, 2 M $K_2CO_3$ solution, is added and the reaction mixture is heated at about 90° C. under an inert atmosphere. The reaction mixture is cooled to room temperature and the product, a compound of formula 103, is isolated and optionally purified.

Referring to Reaction Scheme 1, Step 2, a compound of formula 103, $PdCl_2(dppf)$.DCM and triethylamine are suspended in a suitable solvent, such as degassed MeOH in a vessel fitted with a magnetic stirrer bar. The vessel is pressurised to about 5 bar of CO and heated at about 50° C. with stirring for about 5 hours. The reaction vessel is allowed to cool and the product, a compound of formula 105, is isolated and optionally purified.

Referring to Reaction Scheme 1, Step 3, a compound of formula 105 is suspended in an appropriate solvent such as methanol. Aqueous base, such as aqueous sodium hydroxide, for example, 1M NaOH solution, is added and the reaction mixture is stirred at room temperature for about 4 hours. The product, a compound of formula 107, is isolated and optionally purified.

Referring to Reaction Scheme 1, Step 4, to a solution of a compound of formula 107 in a suitable solvent such as DMF are added EDC.HCl and HOBt. The reaction mixture is stirred at ambient temperature for about 30 minutes after which time an amine of formula $R_2NH_2$ is added. The product, a compound of formula 109, is isolated and optionally purified.

Reaction Scheme 2

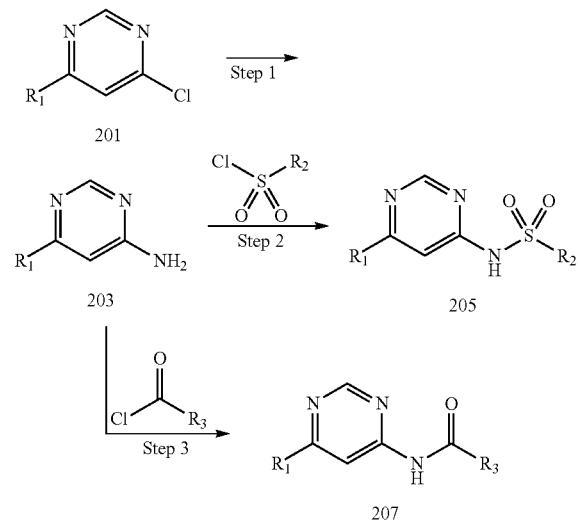

Referring to Reaction Scheme 2, Step 1, a compound of formula 201 is suspended in ammonium hydroxide before irradiation at about 100° C. in a microwave for about 1 hour with stirring. The product, a compound of formula 203, is isolated and optionally purified.

Referring to Reaction Scheme 2, Step 2, a compound of formula 203 is suspended in a suitable solvent such as dioxane. An excess of sodium hydride (such as about 3 to 10 equivalents) is added and the suspension is stirred for about 30 minutes at room temperature. An excess (such as about 1.1 equivalents) of a compound of formula $R_2S(O)_2Cl$ is added and the reaction mixture stirred at room temperature. The product, a compound of formula 205, is isolated and optionally purified.

Referring to Reaction Scheme 2, Step 3, a compound of formula 203 is suspended in an inert solvent such as dioxane. A base such as sodium hydride is added and the suspension is stirred for about 30 minutes at room temperature. An excess (such as about 1.1 equivalents) of the corresponding acid chloride of formula Cl—C(O)—$R_3$ is added and the reaction mixture is stirred at room temperature for about 3 days. Optionally further base may be added. The product, a compound of formula 207, is isolated and optionally purified.

Provided is a method of inhibiting the catalytic activity of KMO, comprising contacting said KMO with an effective amount of at least one chemical entity described herein.

Also provided is a method of treating a condition or disorder mediated by KMO activity in a subject in need of such a treatment, comprising administering to the subject a therapeutically effective amount of at least one chemical entity described herein.

Also provided is a method of treating a neurodegenerative pathology mediated by KMO activity in a subject in need of such a treatment, comprising administering to the subject a therapeutically effective amount of at least one chemical entity described herein. Also provided is a method for treating disorders mediated by (or at least in part by) the presence of KYNA and/or QUIN. Such diseases include, for example, Huntington's disease and other polyglutamine disorders such as spinocerebellar ataxias, Alzheimer's disease, Parkinson's disease, high-pressure neurological syndrome, dystonia, olivopontocerebellar atrophy, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiate withdrawal symptoms, feeding behavior, schizophrenia, chronic anxiety, depressive disorders, disorders of the developing or aged brain, diabetes, and complications thereof, comprising administering to the subject an effective amount of at least one chemical entity described herein.

Also provided are methods of treatment in which at least one chemical entity described herein is the only active agent given to the subject and also includes methods of treatment in which at least one chemical entity described herein is given to the subject in combination with one or more additional active agents.

In general, the chemical entities described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well know to the skilled artisan. The drug can be administered at least once a day, such as once or twice a day.

In some embodiments, the chemical entities described herein are administered as a pharmaceutical composition. Accordingly, provided are pharmaceutical compositions comprising at least one chemical entity described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the chemical entity is sufficient to provide a practical quantity of material for administration per unit dose of the chemical entity.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the chemical entity described herein.

Effective concentrations of at least one chemical entity described herein are mixed with a suitable pharmaceutically acceptable vehicle. In instances in which the chemical entity exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of a chemical entity described herein, the resulting mixture may be a solution, suspension, emulsion or the like. The form of the resulting mixture depends upon a number of factors, including the intended mode of administration and the solubility of the chemical entity in the chosen vehicle. The effective concentration sufficient for ameliorating the symptoms of the disease treated may be empirically determined.

Chemical entities described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one chemical entity described herein. In some embodiments, oral pharmaceutical compositions contain at least 5% (weight %) of at least one chemical entity described herein. Some embodiments contain from 25% to 50% or from 5% to 75% of at least one chemical entity described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

Chemical entities described herein can be incorporated into oral liquid preparations such as aqueous or oily suspensions, solutions, emulsions, syrups, or elixirs, for example. Moreover, pharmaceutical compositions containing these chemical entities can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the chemical entity is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

Chemical entities described herein may be administered parenterally in a sterile medium. Parenteral administration includes subcutaneous injections, intravenous, intramuscular, intrathecal injection or infusion techniques. Chemical entities described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

Chemical entities described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Chemical entities described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. Chemical entities described herein may also be formulated for transdermal administration as a transdermal patch.

Topical pharmaceutical compositions comprising at least one chemical entity described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The chemical entities described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the chemical entity include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the chemical entities described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one chemical entity described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one chemical entity described herein, and instructions for using the composition to treat a subject (typically a human patient). In some embodiments, the instructions are for using the pharmaceutical composition to treat a subject suffering a condition or disorder mediated by Kynurenine 3-mono-oxygenase activity. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the chemical entities can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one chemical entity described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one chemical entity described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are packaged pharmaceutical compositions containing a pharmaceutical composition comprising at least one chemical entity described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for treating Parkinson's disease, including treating memory and/or cognitive impairment associated with Parkinson's disease, comprising administering to a subject, simultaneously or sequentially, at least one chemical entity described herein and one or more additional agents used in the treatment of Parkinson's disease such as, but not limited to, Levodopa, Parlodel, Permax, Mirapex, Tasmar, Contan, Kemadin, Artane, and Cogentin. In methods using simultaneous administration, the agents can be present in a combined composition or can be administered separately. Also provided are pharmaceutical compositions comprising at least one chemical entity described herein, and one or more additional pharmaceutical agents used in the treatment of Parkinson's disease, such as, but not limited to, Levodopa, Parlodel, Permax, Mirapex, Tasmar, Contan, Kemadin, Artane, and Cogentin. Also provided are packaged pharmaceutical compositions containing a pharmaceutical composition comprising at least one chemical entity described herein, and another composition comprising one or more additional pharmaceutical agents gent used in the treatment of Parkinson's disease such as, but not limited to, Levodopa, Parlodel, Permax, Mirapex, Tasmar, Contan, Kemadin, Artane, and Cogentin.

Also provided are methods for treating memory and/or cognitive impairment associated with Alzheimer's disease, comprising administering to a subject, simultaneously or sequentially, at least one chemical entity described herein and one or more additional agents used in the treatment of Alzheimer's disease such as, but not limited to, Reminyl, Cognex, Aricept, Exelon, Akatinol, Neotropin, Eldepryl, Estrogen and Cliquinol. In methods using simultaneous administration, the agents can be present in a combined composition or can be administered separately. Also provided are pharmaceutical compositions comprising at least one chemical entity described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Cliquinol. Similarly, also provided are packaged pharmaceutical compositions containing a pharmaceutical composition comprising at least one chemical entity described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Cliquinol.

Also provided are methods for treating memory and/or cognitive impairment associated with dementia comprising administering to a subject, simultaneously or sequentially, at least one chemical entity and one or more additional agents used in the treatment of dementia such as, but not limited to, Thioridazine, Haloperidol, Risperidone, Cognex, Aricept, and Exelon. In methods using simultaneous administration, the agents can be present in a combined composition or can be administered separately. Also provided are pharmaceutical compositions comprising at least one chemical entity described herein, and one or more additional pharmaceutical agents used in the treatment of dementia such as, but not limited to, Thioridazine, Haloperidol, Risperidone, Cognex, Aricept, and Exelon. Also provided are packaged pharmaceutical compositions containing a pharmaceutical composition comprising at least one chemical entity described herein, and another composition comprising one or more additional pharmaceutical agents used in the treatment of dementia such as, but not limited to, Thioridazine, Haloperidol, Risperidone, Cognex, Aricept, and Exelon.

Also provided are methods for treating memory and/or cognitive impairment associated with epilepsy comprising administering to a subject, simultaneously or sequentially, at least one chemical entity described herein and one or more additional agents used in the treatment of epilepsy such as, but not limited to, Dilantin, Luminol, Tegretol, Depakote, Depakene, Zarontin, Neurontin, Barbita, Solfeton, and Felbatol. In methods using simultaneous administration, the agents can be present in a combined composition or can be administered separately. Also provided are pharmaceutical compositions comprising at least one chemical entity described herein, and one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol. Also provided are packaged pharmaceutical compositions containing a pharmaceutical composition comprising at least one chemical entity described herein, and another composition comprising one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol.

Also provided are methods for treating memory and/or cognitive impairment associated with multiple sclerosis comprising administering to a subject, simultaneously or sequentially, at least one chemical entity described herein and one or more additional agents used in the treatment of multiple sclerosis such as, but not limited to, Detrol, Ditropan XL, OxyContin, Betaseron, Avonex, Azothioprine, Methotrexate, and Copaxone. In methods using simultaneous administration, the agents can be present in a combined composition or can be administered separately. Also provided are pharmaceutical compositions comprising at least one chemical entity described herein, and one or more additional pharmaceutical agents used in the treatment of multiple sclerosis such as, but not limited to, Detrol, Ditropan XL, OxyContin, Betaseron, Avonex, Azothioprine, Methotrexate, and Copaxone. Also provided are packaged pharmaceutical compositions containing a pharmaceutical composition comprising at least one chemical entity described herein, and another composition comprising one or more additional pharmaceutical agents used in the treatment of multiple sclerosis such as, but not limited to, Detrol, Ditropan XL, OxyContin, Betaseron, Avonex, Azothioprine, Methotrexate, and Copaxone.

When used in combination with one or more additional pharmaceutical agent or agents, the described herein may be administered prior to, concurrently with, or following administration of the additional pharmaceutical agent or agents.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The chemical entities described herein are typically administered at dosage levels and in a manner customary for KMO inhibitors. For example, the chemical entities can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one chemical entity described herein, for example, 0.1-50 mg of at least one chemical entity described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one chemical entity described herein.

A labeled form of a chemical entity described herein can be used as a diagnostic for identifying and/or obtaining compounds that have the function of modulating an activity of KMO as described herein. The chemical entities described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The chemical entities, compositions, and methods described herein are further illustrated by the following non-limiting examples.

As used herein, the following abbreviations have the following meanings. If an abbreviation is not defined, it has its generally accepted meaning.

CDI=carbonyldiimidazole
DCM=dichloromethane
DME=dimethyl ether
DMEM=Dulbecco's modified Eagle's medium
DMF=N,N-dimethylformamide
DMSO=dimethylsulfoxide
EDC.HCl=1-Ethyl-3-(3-dimethylaminopropyl)carbodiimide hydrochloride
EtOH=ethanol
Et$_2$O=diethylether
EtOAc=ethyl acetate
g=gram
hr=hour
hrs=hours
HOBt=tert-butyl alcohol
LiHMDS=lithium hexamethyl-disilazide
LC/MS=liquid chomatography/mass spectrometry
mg=milligram
min=minutes
mL=milliliter
mmol=millimoles
mM=millimolar
ng=nanogram
nm=nanometer
nM=nanomolar
PBS=phosphate buffered saline
rt=room temperature
TBME=t-butyl methyl ether
THF=tetrahydrofuran
TMOF=trimethylorthoformate μL=microliter
μM=micromolar Experimental Commercially available reagents and solvents (HPLC grade) were used without further purification.

Thin-layer chromatography (TLC) analysis was performed with Kieselgel 60 $F_{254}$ (Merck) plates and visualized using UV light. Microwave reactions were carried out using CEM focussed microwaves.

Analytical HPLC-MS was performed on Agilent HP1100 and Shimadzu 2010, systems using reverse phase Atlantis dC18 columns (5 μm, 2.1×50 mm), gradient 5-100% B (A=water/0.1% formic acid, B=acetonitrile/0.1% formic acid) over 3 min, injection volume 3 μl, flow=1.0 ml/min. UV spectra were recorded at 215 nm using a Waters 2487 dual wavelength UV detector or the Shimadzu 2010 system. Mass spectra were obtained over the range m/z 150 to 850 at a sampling rate of 2 scans per second using Waters ZMD and over m/z 100 to 1000 at a sampling rate of 2 Hz using Electrospray ionisation, by a Shimadzu 2010 LC-MS system or analytical HPLC-MS was performed on Agilent HP1100 and Shimadzu 2010, systems using reverse phase Water Atlantis dC18 columns (3 μm, 2.1×100 mm), gradient 5-100% B (A=water/0.1% formic acid, B=acetonitrile/0.1% formic acid) over 7 min, injection volume 3 μl, flow=0.6 ml/min. UV spectra were recorded at 215 nm using a Waters 2996 photo diode array or on the Shimadzu 2010 system. Mass spectra were obtained over the range m/z 150 to 850 at a sampling rate of 2 scans per second using Waters ZQ and over m/z 100 to 1000 at a sampling rate of 2 Hz using Electrospray ionisation, by a Shimadzu 2010 LC-MS system. Data were integrated and reported using OpenLynx and OpenLynx Browser software or via Shimadzu PsiPort software.

1 g/1 ml=1 vol

General Procedures

Method A. Amide Coupling.

To a solution of carboxylic acid (1 eq) in DMF were added EDC.HCl (1 eq) and HOBt (1 eq). The reaction mixture was stirred at ambient temperature for 30 minutes after which time the appropriate amine was added. The reaction was monitored by LCMS. After completion the reaction mixture was poured into water after which a precipitate came out of solution and was filtered, washed with water, heptane and dried in vacuo to yield the target compound or if a precipitate was not formed the reaction mixture was extracted with EtOAc (3×) and the combined organic layers were washed with water, saturated aqueous NaCl, dried ($Na_2SO_4$ or $MgSO_4$) and the solvent removed in vacuo to afford the crude product. Purification was carried out by flash column chromatography, prep HPLC, or a combination of both.

Method B. Amide Coupling.

To a solution of carboxylic acid (1 eq) in DCM (20 vol) under nitrogen were added oxalyl chloride (3 eq) and 1 drop of DMF (cat.). The reaction mixture was stirred at ambient temperature for 30 minutes after which time the solvents were removed in vacuo. DCM (20 vol) or THF (20 vol) was added, followed by the required amine (1 to 3 eq) and triethylamine (2 eq) and the reaction mixture was stirred at ambient temperature. The reaction was monitored by LCMS to completion whereupon water was added. The reaction mixture was then extracted with DCM and the organic layer was washed with water, saturated aqueous NaCl, dried over $Na_2SO_4$ or $MgSO_4$ and the solvent removed in vacuo to afford the crude product. Purification was carried out by flash column chromatography, prep HPLC, a combination of both or by trituration with an appropriate solvent.

Example 1

Preparation of Pyrimidine Analogues

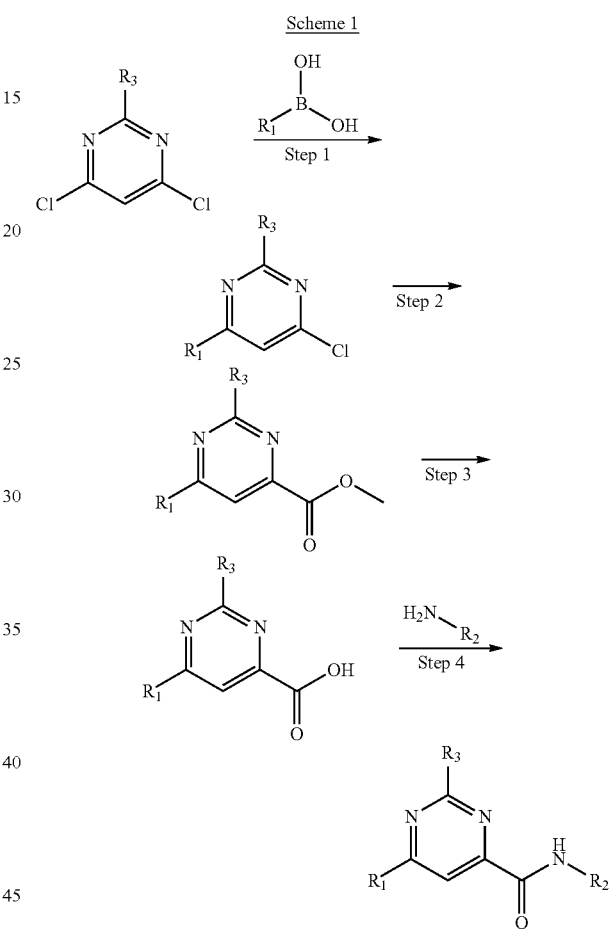

Scheme 1

Stage 1

To a stirred suspension of dichloropyrimidine (1 eq) in 1,4-dioxane (15 vol) was added boronic acid (0.7 eq) and $Pd(PPh_3)_4$ (0.025 eq). A 2M $K_2CO_3$ solution (7.5 vol) was added to the resulting mixture, which was heated at 90° C. overnight under an atmosphere of $N_2$. The reaction mixture was cooled to room temperature and concentrated in vacuo. The residue was dissolved in EtOAc:water (1:1) (100 vol) and the resulting solution filtered through celite. The organic layer was separated and the aqueous layer further extracted with EtOAc (50 vol). The combined organic layers were washed with saturated aqueous NaCl(20 vol), dried over $Na_2SO_4$, filtered and the solvent removed in vacuo. The resulting residue was purified by flash column chromatography (eluent: [0:1 to 1:19]EtOAc:heptane) to afford the required target compounds.

Stage 2

4-Chloro-6-substituted-phenyl-pyrimidine (1 eq), $PdCl_2$ (dppf).DCM (0.05 eq) and triethylamine (2 eq) were suspended in degassed MeOH (50 vol) in a bomb fitted with a magnetic stirrer bar. The atmosphere in the reaction vessel was replaced with $N_2$ by successive evacuation and charging with $N_2$ gas (this process was repeated three times). The bomb was then flushed with CO by successive charging with CO and evacuation. The vessel was pressurised to 5 bar of CO and heated at 50° C. with stirring for 5 hours. The reaction vessel was allowed to cool to room temperature before venting CO and flushing with $N_2$. The reaction mixture was concentrated in vacuo and the resulting residue dissolved in EtOAc (30 vol) and water (30 vol). The solution was filtered through cotton wool and the organic layer was separated, washed with saturated aqueous NaCl(15 vol), dried over $Na_2SO_4$, filtered and concentrated under reduced pressure. Purification by flash column chromatography (eluent: [0:1 to 1:9]EtOAc:heptane) yielded the target compounds.

Stage 3

6-Substituted-phenyl-pyrimidine-4-carboxylic acid methyl ester (1 eq) was suspended in MeOH (20 vol), 1M NaOH solution (20 vol) and stirred at room temperature for 4 hours. The reaction mixture was acidified with 2M HCl. Soluble products were extracted with DCM (2×20 vol) and the combined organic layers were dried over $MgSO_4$, filtered and concentration under reduced pressure afforded the target compounds. Insoluble products were filtered, washed with water (3×10 vol) and heptane (3×10 vol) before drying in vacuo to yield the target compounds.

Stage 4

The required amide analogues were prepared following the procedures described in method A or B.

Example 2

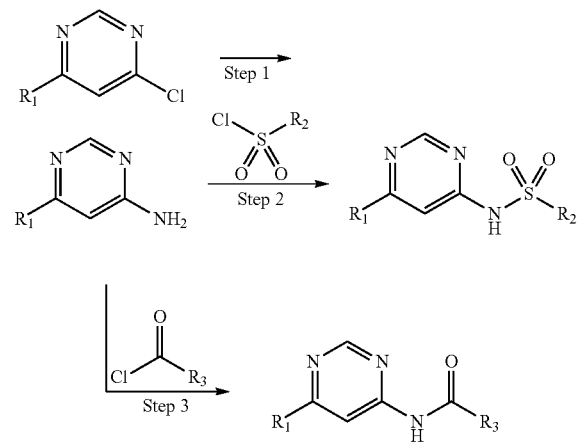

Step 1

4-Chloro-6-substituted-phenyl-pyrimidine (1 eq) was suspended in ammonium hydroxide (60 vol) before irradiation at 100° C. in a microwave for 1 hour with stirring. The reaction mixture was extracted with DCM (5×20 vol). Solvent was removed in vacuo to yield the target compound.

Step 2

6-Substituted-phenyl-pyrimidin-4-ylamine (1 eq) was suspended in dioxane (30 vol). Sodium hydride (3 to 10 eq) was added and the suspension stirred for 30 minutes at room temperature. The corresponding sulfonyl chloride (1.1 eq) was added and the reaction mixture stirred at room temperature for 1 to 5 days. The reaction was quenched by the addition of water (40 vol), EtOAc (40 vol) was added and the mixture partitioned. The aqueous layer was washed with EtOAc (3×20 vol) and the organic layer discarded. The aqueous layer was then acidified to ~pH1 with concentrated HCl and extracted with EtOAc (4×40 vol). The combined organic layers were washed with saturated aqueous NaCl solution (40 vol), dried over $Na_2SO_4$, filtered and concentrated in vacuo to afford the target compounds.

Step 3

6-Substituted-phenyl-pyrimidin-4-ylamine (1 eq) was suspended in dioxane (20 vol). Sodium hydride (4 eq) was added and the suspension stirred for 30 minutes at room temperature. The corresponding acid chloride (1.1 eq) was added and the reaction mixture stirred at room temperature for 3 days. A further addition of sodium hydride (4 eq) was required and the reaction mixture stirred at room temperature for 24 h. The reaction was quenched by the addition of water (75 vol), and acidified with HCl (to pH1). The acidic solution was extracted with DCM (2×50 vol). The combined organic layers were washed with saturated aqueous NaCl solution (50 vol), dried over $Na_2SO_4$, filtered and concentrated in vacuo. The residue was recrystallised from hot MeOH to afford the target compound.

Example 3

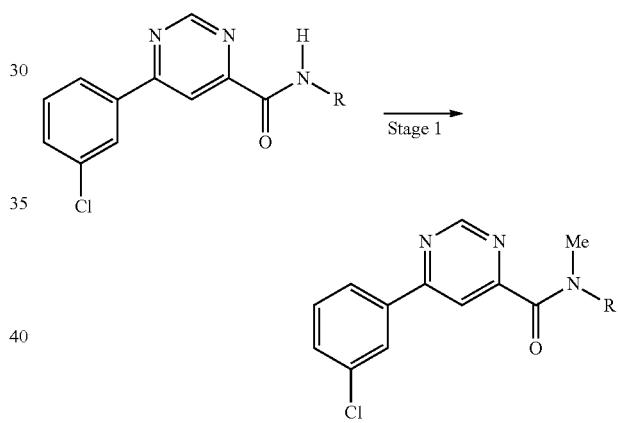

To a stirred solution of 6-(3-chloro-phenyl)-pyrimidine-4-carboxylic acid amide (1 eq) in DMF (25 vol) was added sodium hydride (1.1 eq). The reaction mixture was stirred at ambient temperature for 30 mins and methyl iodide (2 eq) was added. The reaction mixture was stirred at ambient temperature for 3 to 4 hours. Water was added and the mixture was extracted with ethyl acetate or DCM. The organic layer was washed with water and brine, dried over $MgSO_4$, filtered and the solvent removed in vacuo to furnish the crude amide, which was further purified by flash column chromatography or prep HPLC.

Example 4

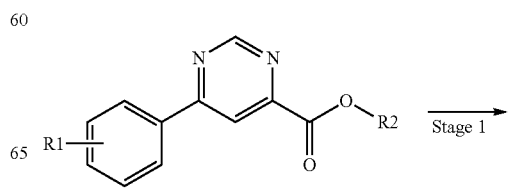

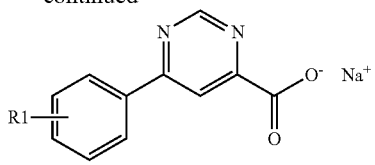

To a stirred solution of 6-(3-chloro-phenyl)-pyrimidine-4-carboxylic acid (1 eq) or 6-(3,4-dichloro-phenyl)-pyrimidine-4-carboxylic acid methyl ester in THF (20 vol) was added dropwise a 1M NaOH solution. The mixture was stirred at ambient temperature and the resulting precipitate was filtered and washed with water/THF or with water then heptane to furnish the described salts.

Example 5

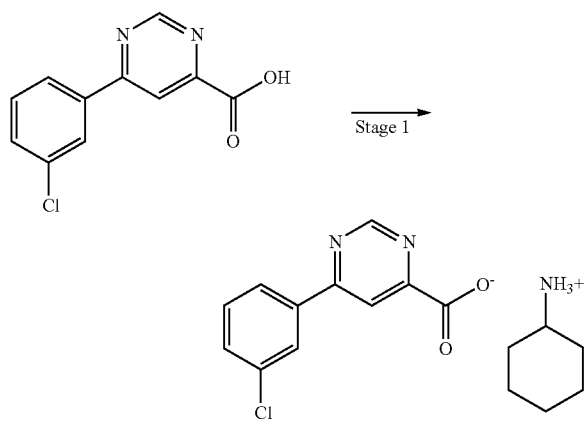

To a stirred solution of 6-(3-chloro-phenyl)-pyrimidine-4-carboxylic acid (1 eq) dissolved in the minimum amount of THF was added cyclohexylamine. The mixture was stirred at ambient temperature for 1 hour and the resulting precipitate was filtered and washed with THF to furnish the described salt.

Example 6

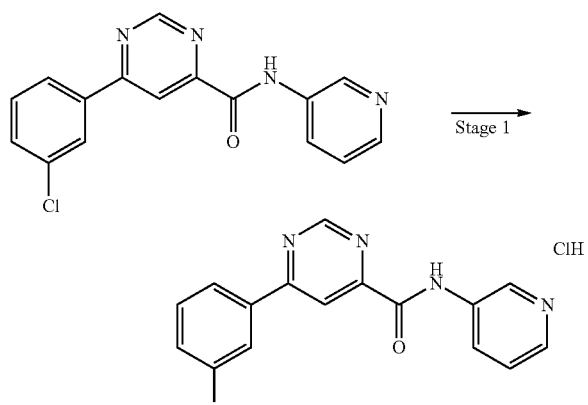

To a stirred suspension of 6-(3-chloro-phenyl)-pyrimidine-4-carboxylic acid pyridin-3-ylamide (1 eq) in methanol was added 6N HCl at ambient temperature. After complete dissolution was observed, the solvents were removed in vacuo and the resulting salt was purified by successive trituration with acetone and tert-butylmethylether. Re-crystallisation from ethanol afforded the desired compound.

Example 7

Stage 1

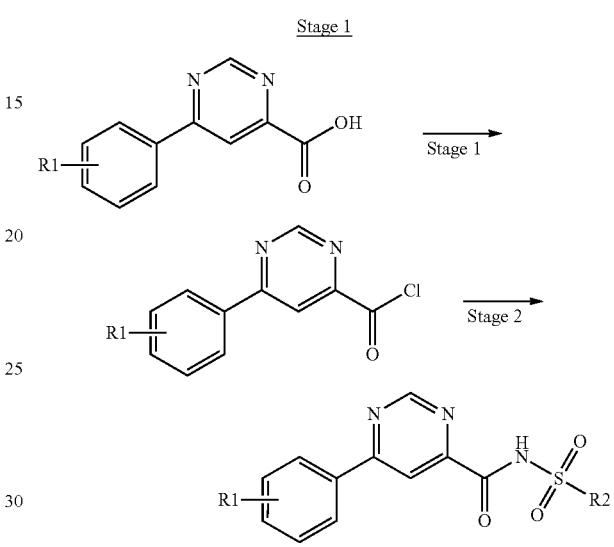

To a stirred solution of 6-(substituted-phenyl)-pyrimidine-4-carboxylic acid (1 eq) in DCM (20 vol) under an atmosphere of nitrogen were added oxalyl chloride (3 eq) and 1 drop of DMF (cat.). The reaction mixture was stirred at ambient temperature for 30 minutes after which time the solvents were removed in vacuo. The resulting residue was used in the next stage without further purification.

Stage 2

The resulting residue was dissolved in THF (10 vol). Triethylamine (1 eq) and the appropriate sulfonamide (1.5 eq) were added to the reaction mixture, which was stirred at ambient temperature for 4 to 16 hours. The solvent was removed in vacuo and the resulting residue was purified by trituration with water and diethyl ether. The solid was filtered and washed with water and DCM. When precipitation did not happen, the solvent was removed in vacuo and DCM was added. The organic phase was washed with a saturated solution of sodium bicarbonate followed by a 2M solution of citric acid, dried with Na$_2$SO$_4$, filtered and the solvent removed in vacuo to furnish the crude compound, which was purified by flash column chromatography (eluent: [1:10] to [1:0]EtOAc:heptane) to furnish the desired target compound.

Example 8

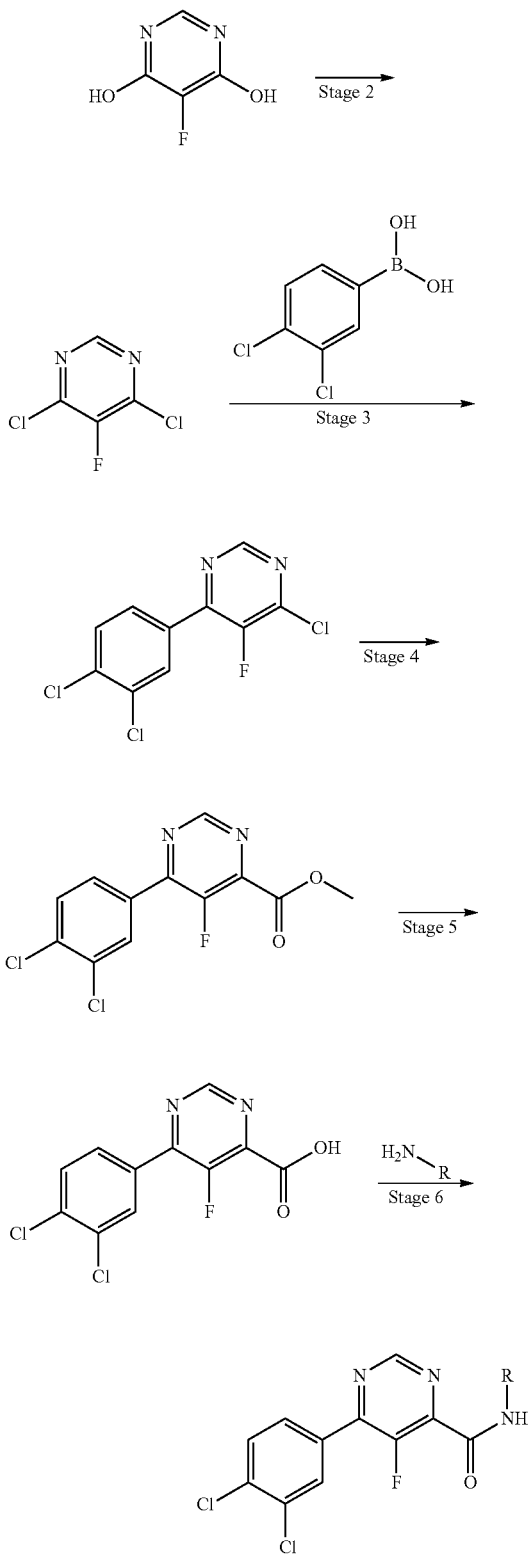

Stage 1

To a stirred solution of formamidine acetate (1 eq) in ethanol (50 vol) was added a solution of sodium ethoxide in ethanol (2% w/w) (3 eq) at 0° C. and the reaction mixture was stirred at that temperature for 30 minutes. To the resulting mixture was added a solution of diethyl fluoromalonate (1 eq) in ethanol (5 vol) and the reaction mixture was stirred at ambient temperature for 72 hours. The reaction mixture was cooled to 0° C. and concentrated HCl (3 vol) was added to adjust the pH of the reaction mixture to pH6. The resulting precipitate was filtered, washed with isopropanol, diethyl-ether and hexane to furnish the desired intermediate, which was used in the next stage without further purification.

Stage 2

To a stirred solution of N,N-dimethylaniline (1 eq) in phosphorous oxychloride (4 vol) was added 5-fluoro-pyrimidine-4,6-diol (1 eq) and the reaction mixture was heated at reflux for 16 hours. After cooling to room temperature the solvent was removed in vacuo and the resulting residue was poured into ice. The desired intermediate was then extracted with EtOAc. The organic layer was dried with MgSO$_4$, filtered and the solvent removed in vacuo to furnish the desired intermediate, which was used in the next stage without further purification.

Stage 3

4,6-Dichloro-5-fluoro-pyrimidine (1 eq), 3,4-dichlorophenyl boronic acid (0.7 eq) and Pd(PPh$_3$)$_4$ (0.05 eq) were suspended in 1,4-dioxane (20 vol). A 2M K$_2$CO$_3$ solution (6.75 vol) was added and the reaction mixture was heated at 90° C. with stirring for 2 hours under an atmosphere of N$_2$. The reaction mixture was cooled to room temperature and concentrated in vacuo. The residue was dissolved in EtOAc and water. The mixture was partitioned and the aqueous layer further extracted with EtOAc. The combined organic layers were washed with saturated aqueous NaCl, dried over Na$_2$SO$_4$, filtered and the solvent removed in vacuo. The resulting residue was purified by flash column chromatography (eluent: [1:15]EtOAc:heptane) to afford the required target compound.

Stage 4

4-Chloro-6-(3,4-dichloro-phenyl)-5-fluoro-pyrimidine (1 eq), PdCl$_2$(dppf).DCM (0.05 eq) and triethylamine (2 eq) were suspended in degassed MeOH (50 vol) in a bomb fitted with a magnetic stirrer bar. The atmosphere in the reaction vessel was replaced with N$_2$ by successive evacuation and charging with N$_2$ gas (this process was repeated three times). The bomb was then flushed with CO by successive charging with CO and evacuation. The vessel was pressurised to 5 bar of CO and heated at 50° C. with stirring for 5 hours. The reaction vessel was allowed to cool to room temperature before venting CO and flushing with N$_2$. The reaction mixture was concentrated in vacuo. Purification of the residue by flash column chromatography (eluent: [1:15]EtOAc:heptane) yielded the target compound.

Stage 5

6-(3,4-Dichloro-phenyl)-5-fluoro-pyrimidine-4-carboxylic acid methyl ester (1 eq) was suspended in THF (30 vol), 2M NaOH solution (5 eq) and stirred at room temperature for 3 hours. The reaction mixture was concentrated in vacuo. The resulting residue was dissolved in EtOAc and water. The aqueous layer was separated and the precipitate removed by filtration. The aqueous layer was acidified with conc. HCl and the resulting precipitate was filtered and washed with water to furnish the desired target compound.

Stage 6

The required amide analogues were prepared following the procedure described in method B and were purified by trituration in acetonitrile/water (1/1).

Example 9

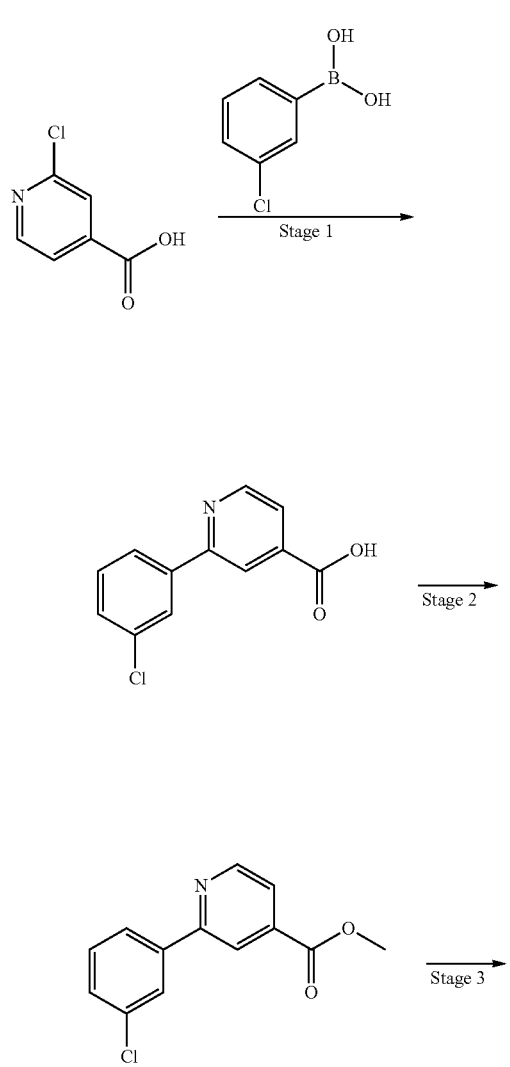

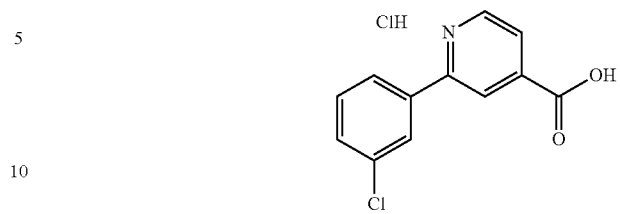

Stage 1

2-Chloro-isonicotinic acid (1 eq), 3-chlorophenyl boronic acid (1.5 eq) and Pd(PPh$_3$)$_4$ (0.03 eq) were suspended in 1,4-dioxane (20 vol). A 2M K$_2$CO$_3$ solution (7.5 vol) was added to the reaction mixture, which was heated at 90° C. with stirring for 16 hours under an atmosphere of N$_2$. 3-Chlorophenyl boronic acid (0.5 eq), Pd(PPh$_3$)$_4$ (0.03 eq) and a 2M K$_2$CO$_3$ solution (7.5 vol) were added to the reaction mixture, which was heated at 90° C. for a further hour. The reaction mixture was cooled to room temperature and washed with EtOAc and dichloromethane. The aqueous layer was acidified with concentrated HCl and the resulting precipitate was isolated by filtration and used in the next step without further purification.

Stage 2

To a stirred suspension of the intermediate obtained in Stage 1 in methanol (50 vol) was added concentrated HCl (4 drops) and the reaction mixture was stirred at 65° C. for 16 hours. The reaction mixture was concentrated in vacuo. The resulting residue was dissolved in DCM and water. The organic phase was collected and the solvent was removed in vacuo. Purification by flash column chromatography (eluent: [1:20]EtOAc:heptane), followed by prep HPLC yielded the target compound.

Stage 3

To a stirred solution of 2-(3-chloro-phenyl)-isonicotinic acid methyl ester (1 eq) in THF (30 vol) was added 2M NaOH solution (8 vol) and the reaction mixture was stirred at ambient temperature for 3 hours. The reaction mixture was concentrated in vacuo. The residue was dissolved in a 2M solution of HCl and the resulting precipitate was filtered off and washed with water and heptane to furnish the desired target compound.

Example 10

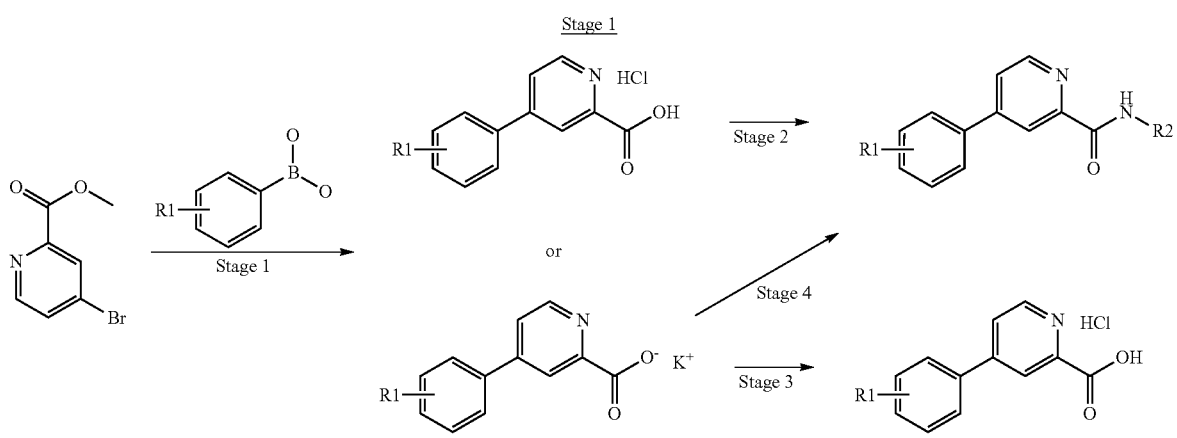

To a stirred suspension of 4-bromo-pyridine-2-carboxylic acid methyl ester (1 eq) in 1,4-dioxane (20 vol) was added the appropriate substituted phenyl boronic acid (1.1 eq) and Pd(PPh$_3$)$_4$ (0.05 eq). A 2M K$_2$CO$_3$ solution (7.5 vol) was added and the reaction mixture was heated at 90° C. with stirring for 16 hours under an atmosphere of N$_2$. The reaction mixture was cooled to room temperature and the resulting precipitate was isolated by filtration to furnish the acid intermediate as the potassium salt, which was used without further purification in the stage. In the case of the 3-chlorophenyl analogue no precipitate was formed upon cooling, hence the solvent was removed in vacuo. The resulting residue was dissolved in EtOAc and water. Both phases were separated. EtOAc was removed in vacuo and the resulting residue was purified by flash column chromatography (eluent: [5:95] methanol:DCM) to furnish the desired 4-(3-chloro-phenyl)-pyridine-2-carboxylic acid methyl ester. The aqueous phase was acidified and the resulting precipitate was isolated by filtration and used as such in stage 2. Further purification was carried out by prep HPLC to furnish the required 4-(3-chloro-phenyl)-pyridine-2-carboxylic acid.

Stage 2

The required amide analogues were prepared following the procedure described in method A from 4-(3-chloro-phenyl)-pyridine-2-carboxylic acid, hydrochloride salt and were purified by trituration in acetonitrile/water (1/1) or in water followed by heptane.

Stage 3

The potassium salt isolated in stage 1 was suspended in HCl (2M) and stirred at ambient temperature for 2 hours. The solid was filtered and washed with water to furnish the desired target compound.

Stage 4

The required amide analogues were prepared following the procedure described in method A from 4-(substituted-phenyl)-pyridine-2-carboxylic acid potassium salt and were purified by trituration in acetonitrile/water (1/1) or in water followed by heptane.

Example 11

The following compounds were prepared substantially as described above.

| IUPAC name | Mass Spec Result |
|---|---|
| 6-(2-Trifluoromethyl-phenyl)-pyrimidine-4-carboxylic acid methyl ester | [M + H]$^+$ = 283, 94% @ rt = 3.90 min |
| 6-(2-Trifluoromethyl-phenyl)-pyrimidine-4-carboxylic acid | [M + H]$^+$ = 269, 100% @ rt = 3.34 min |
| N-[6-(2-Trifluoromethyl-phenyl)-pyrimidin-4-yl]-methanesulfonamide | [M + H]$^+$ = 311, 98% @ rt = 4.00 min |
| 3,4-Dimethoxy-N-[6-(2-trifluoromethyl-phenyl)-pyrimidin-4-yl]-benzenesulfonamide | [M + H]$^+$ = 318, 98% @ rt = 3.92 min |
| N-[6-(3,4-Dichloro-phenyl)-pyrimidin-4-yl]-methanesulfonamide | [M + H]$^+$ = 440, 100% @ rt = 4.41 min |
| 6-(3,4-Dichloro-phenyl)-pyrimidine-4-carboxylic acid methyl ester | [M + H]$^+$ = 283, 100% @ rt = 4.47 min |
| N-[6-(3,4-Dichloro-phenyl)-pyrimidin-4-yl]-3,4-dimethoxy-benzenesulfonamide | [M + H]$^+$ = 440, 100% @ rt = 3.88 min |
| 6-(3-Chloro-phenyl)-pyrimidine-4-carboxylic acid methyl ester | [M + H]$^+$ = 249, 97% @ rt = 3.98 min |
| 6-(3-Chloro-phenyl)-pyrimidine-4-carboxylic acid | [M + H]$^+$ = 235, 100% @ rt = 3.66 min |
| 6-(3-chloro-phenyl)-pyrimidine-4-carboxylic acid sodium salt | [M + H]$^+$ = 235, 89% @ rt = 3.93 min |
| 6-(3-Chloro-phenyl)-pyrimidine-4-carboxylic acid cyclohexyl ammonium salt | [M + H]$^+$ = 235, 92% @ rt = 3.84 min |
| 6-(3,4-Dichloro-phenyl)-pyrimidine-4-carboxylic acid pyridin-3-ylamide | [M + H]$^+$ = 345, 95% @ rt = 4.17 min |
| 6-(3-Chloro-phenyl)-pyrimidine-4-carboxylic acid pyridin-3-ylamide | [M + H]$^+$ = 311, 100% @ rt = 3.74 min |
| 6-(3-Chloro-phenyl)-pyrimidine-4-carboxylic acid pyridin-3-ylamide hydrochloride salt | [M + H]$^+$ = 311, 100% @ rt 3.73 min |
| 6-(3,4-Dichloro-phenyl)-pyrimidine-4-carboxylic acid | [M + H]$^+$ = 269, 100% @ rt = 4.04 min |
| 6-(3,4-dichloro-phenyl)-pyrimidine-4-carboxylic acid sodium salt | [M + H]$^+$ = 269/271, 100% @ rt = 4.17 min |
| 6-(3,5-Dichloro-phenyl)-pyrimidine-4-carboxylic acid | [M + H]$^+$ = 269, 99% @ rt = 4.30 min |
| 6-(3,5-Dichloro-phenyl)-pyrimidine-4-carboxylic acid methyl ester | [M + H]$^+$ = 283, 99% @ rt = 4.58 min |
| N-[6-(3-Chloro-phenyl)-pyrimidin-4-yl]-nicotinamide | [M + H]$^+$ = 318, 94% @ rt = 3.39 min |
| 6-(3,4-Dichloro-phenyl)-2-methyl-pyrimidine-4-carboxylic acid methyl ester | [M + H]$^+$ = 297, 100% @ rt = 4.78 min |
| 6-(3,4-Dichloro-phenyl)-2-methyl-pyrimidine-4-carboxylic acid | [M + H]$^+$ = 283, 99% @ rt = 4.43 min |
| 6-(3,4-Dichloro-phenyl)-2-methyl-pyrimidine-4-carboxylic acid pyridin-3-ylamide | [M + H]$^+$ = 359, 100% @ rt = 4.50 min |
| 6-(3-Chloro-phenyl)-pyrimidine-4-carboxylic acid (2,6-dimethyl-pyridin-3-yl)-amide | [M + H]$^+$ = 339, 100% @ rt = 3.17 min |

-continued

| IUPAC name | Mass Spec Result |
|---|---|
| 6-(3-Chloro-phenyl)-pyrimidine-4-carboxylic acid pyrimidin-5-ylamide | $[M + H]^+$ = 312, 98% @ rt = 4.00 min |
| 6-(4-Morpholin-4-yl-phenyl)-pyrimidine-4-carboxylic acid methyl ester | $[M + H]^+$ = 300, 96% @ rt = 3.61 min |
| 6-(4-Fluoro-3-trifluoromethyl-phenyl)-pyrimidine-4-carboxylic acid methyl ester | $[M + H]^+$ = 300, 95% @ rt = 4.39 min |
| 6-(3-Trifluoromethyl-phenyl)-pyrimidine-4-carboxylic acid methyl ester | $[M + H]^+$ = 282, 97% @ rt = 4.16 min |
| 6-(4-Fluoro-3-trifluoromethyl-phenyl)-pyrimidine-4-carboxylic acid | $[M + H]^+$ = 286, 100% @ rt = 4.07 min |
| 6-(3-Trifluoromethyl-phenyl)-pyrimidine-4-carboxylic acid pyridin-2-ylamide | $[M + H]^+$ = 345, 100% @ rt = 4.92 min |
| 6-(4-Fluoro-3-trifluoromethyl-phenyl)-pyrimidine-4-carboxylic acid pyridin-3-ylamide | $[M + H]^+$ = 363, 99% @ rt = 4.06 min |
| 6-(3,5-Dichloro-phenyl)-pyrimidine-4-carboxylic acid pyridin-3-ylamide | $[M + H]^+$ = 344, 100% @ rt = 4.38 min |
| 6-(3-Trifluoromethyl-phenyl)-pyrimidine-4-carboxylic acid pyridin-3-ylamide | $[M + H]^+$ = 344, 100% @ rt = 3.89 min |
| 6-(3-Trifluoromethyl-phenyl)-pyrimidine-4-carboxylic acid | $[M + H]^+$ = 268, 100% @ rt = 3.78 min |
| 6-(3-Chloro-phenyl)-pyrimidine-4-carboxylic acid ethylamide | $[M + H]^+$ = 262, 99% @ rt = 4.34 min |
| 6-(5-Fluoro-pyridin-3-yl)-pyrimidine-4-carboxylic acid | $[M + H]^+$ = 219, 99% @ rt = 2.66 min |
| 6-(3-Chloro-phenyl)-pyrimidine-4-carboxylic acid amide | $[M + H]^+$ = 234, 100% @ rt = 3.60 min |
| 6-(3-Fluoro-5-trifluoromethyl-phenyl)-pyrimidine-4-carboxylic acid methyl ester | $[M + H]^+$ = 300, 100% @ rt = 4.52 min |
| 6-(3-Chloro-phenyl)-pyrimidine-4-carboxylic acid methylamide | $[M + H]^+$ = 248, 100% @ rt = 3.85 min |
| 6-(5-Fluoro-pyridin-3-yl)-pyrimidine-4-carboxylic acid methyl ester | $[M + H]^+$ = 233, 100% @ rt = 2.96 min |
| 6-(3-Fluoro-5-trifluoromethyl-phenyl)-pyrimidine-4-carboxylic acid | $[M + H]^+$ = 286, 97% @ rt = 4.26 min |
| 6-(5-Chloro-pyridin-3-yl)-pyrimidine-4-carboxylic acid methyl ester | $[M + H]^+$ = 249, 100% @ rt = 3.30 min |
| 6-(5-Chloro-pyridin-3-yl)-pyrimidine-4-carboxylic acid | $[M + H]^+$ = 236, 100% @ rt = 2.92 min |
| 6-(2-Fluoro-5-trifluoromethyl-phenyl)-pyrimidine-4-carboxylic acid methyl ester | $[M + 23]^+$ = 301, 100% @ rt = 4.17 min |
| 6-(3-Chloro-phenyl)-pyrimidine-4-carboxylic acid isopropylamide | $[M + H]^+$ = 275, 99% @ rt = 4.68 min |
| [6-(3-Chloro-phenyl)-pyrimidin-4-yl]-morpholin-4-yl-methanone | $[M + H]^+$ = 304, 100% @ rt = 3.64 min |
| 6-(3-Chloro-phenyl)-pyrimidine-4-carboxylic acid propylamide | $[M + H]^+$ = 276, 100% @ rt = 4.39 min |
| 6-(3-Chloro-phenyl)-pyrimidine-4-carboxylic acid phenylamide | $[M + H]^+$ = 309, 100% @ rt = 5.17 min |
| 6-Pyridin-3-yl-pyrimidine-4-carboxylic acid methyl ester trifluoroacetic acid salt | $[M + H]^+$ = 216, 100% @ rt = 2.27 min |
| 6-Phenyl-pyrimidine-4-carboxylic acid | $[M + H]^+$ = 201, 100% @ rt = 3.29 min |
| 6-(2-Fluoro-5-trifluoromethyl-phenyl)-pyrimidine-4-carboxylic acid | $[M + H]^+$ = 286, 100% @ rt = 4.03 min |
| 6-(3-Chloro-phenyl)-pyrimidine-4-carboxylic acid o-tolylamide | $[M + H]^+$ = 324, 100% @ rt = 5.08 min |
| 6-(3-Chloro-phenyl)-pyrimidine-4-carboxylic acid p-tolylamide | $[M + H]^+$ = 323, 100% @ rt = 5.40 min |
| [6-(3-Chloro-phenyl)-pyrimidin-4-yl]-(3,4-dihydro-2H-quinolin-1-yl)-methanone | $[M + H]^+$ = 350/352, 100% @ rt = 4.57 min |
| 6-Phenyl-pyrimidine-4-carboxylic acid methyl ester | $[M + H]^+$ = 215, 99% @ rt = 3.55 min |
| 6-(2,4-Difluoro-phenyl)-pyrimidine-4-carboxylic acid methyl ester | $[M + H]^+$ = 251, 98% @ rt = 3.76 min |
| 6-(2,4-Difluoro-phenyl)-pyrimidine-4-carboxylic acid | $[M + H]^+$ = 237, 100% @ rt = 3.41 min |
| 6-(3-Chloro-phenyl)-pyrimidine-4-carboxylic acid (6-methoxy-pyridin-3-yl)-amide | $[M + H]^+$ = 341, 100% @ rt = 4.53 min |
| [6-(3-Chloro-phenyl)-pyrimidin-4-yl]-(2,3-dihydro-indol-1-yl)-methanone | $[M + H]^+$ = 336, 100% @ rt = 4.57 min |
| 6-(3-Chloro-phenyl)-pyrimidine-4-carboxylic acid m-tolylamide | $[M + H]^+$ = 324, 100% @ rt = 5.25 min |
| 6-(3-Chloro-phenyl)-pyrimidine-4-carboxylic acid methyl-pyridin-3-yl-amide | $[M + H]^+$ = 325, 100% @ rt = 3.71 min |
| 6-(3-Chloro-phenyl)-pyrimidine-4-carboxylic acid (5-methoxy-pyridin-3-yl)-amide | $[M + H]^+$ = 341, 100% @ rt = 4.15 min |

-continued

| IUPAC name | Mass Spec Result |
|---|---|
| 6-(3-Chloro-2-fluoro-phenyl)-pyrimidine-4-carboxylic acid methyl ester | [M + H]$^+$ = 267, 100% @ rt = 3.99 min |
| 6-(3-Chloro-phenyl)-pyrimidine-4-carboxylic acid dimethylamide | [M + H]$^+$ = 262, 100% @ rt = 3.73 min |
| 6-(3-Chloro-phenyl)-2-methyl-pyrimidine-4-carboxylic acid methyl ester | [M + H]$^+$ = 262, 99% @ rt = 4.48 min |
| 4-[6-(3-Chloro-phenyl)-pyrimidine-4-carbonyl]-piperazin-2-one | [M + H]$^+$ = 317, 100% @ rt = 3.30 min |
| 6-Phenyl-pyrimidine-4-carboxylic acid pyridin-3-ylamide | [M + H]$^+$ = 277, 100% @ rt = 3.30 min |
| 6-(3-Chloro-2-fluoro-phenyl)-pyrimidine-4-carboxylic acid | [M + H]$^+$ = 253, 97% @ rt = 3.96 min |
| 6-(3,4-Dichloro-phenylamino)-pyrimidine-4-carboxylic acid methyl ester | [M + H]$^+$ = 297, 100% @ rt = 4.21 min |
| 6-(3-Chloro-phenyl)-pyrimidine-4-carboxylic acid (4-methoxy-pyridin-3-yl)-amide | [M + H]$^+$ = 341, 99% @ rt = 3.19 min |
| 6-(3-Chloro-phenyl)-2-methyl-pyrimidine-4-carboxylic acid | [M + H]$^+$ = 249, 100% @ rt = 3.88 min |
| 6-(3-Chloro-phenyl)-2-methyl-pyrimidine-4-carboxylic acid pyridin-3-ylamide | [M + H]$^+$ = 325, 100% @ rt = 4.14 min |
| 6-(3-Chloro-phenyl)-pyrimidine-4-carboxylic acid (2-hydroxy-ethyl)-amide | [M + H]$^+$ = 278, 100% @ rt = 3.56 min |
| [6-(3-Chloro-phenyl)-pyrimidin-4-yl]-(4-hydroxy-piperidin-1-yl)-methanone | [M + H]$^+$ = 318, 100% @ rt = 3.42 min |
| 6-(3-Methoxy-phenyl)-pyrimidine-4-carboxylic acid | [M + H]$^+$ = 231, 100% @ rt = 3.20 min |
| 6-(3-Methoxy-phenyl)-pyrimidine-4-carboxylic acid methyl ester | [M + H]$^+$ = 245, 99% @ rt = 3.80 min |
| 6-(3-Chloro-phenyl)-pyrimidine-4-carboxylic acid benzylamide | [M + H]$^+$ = 324, 100% @ rt = 4.97 min |
| 6-Morpholin-4-yl-pyrimidine-4-carboxylic acid hydochloride salt | [M + H]$^+$ = 210, 100% @ rt 1.02 min - LCMS profile of distorted appearance |
| [6-(3-Chloro-phenyl)-pyrimidin-4-yl]-(4-methyl-piperazin-1-yl)-methanone | [M + H]$^+$ = 317, 100% @ rt = 2.66 min |
| [6-(3-Chloro-phenyl)-pyrimidin-4-yl]-pyrrolidin-1-yl-methanone | [M + H]$^+$ = 287, 100% @ rt = 4.56 min |
| 6-(3-Chloro-phenyl)-pyrimidine-4-carboxylic acid ((S)-2-hydroxy-propyl)-amide | [M + H]$^+$ = 292, 100% @ rt = 3.78 min |
| 6-m-Tolyl-pyrimidine-4-carboxylic acid methyl ester | [M + H]$^+$ = 229, 100% @ rt = 4.06 min |
| 1-{4-[6-(3-Chloro-phenyl)-pyrimidine-4-carbonyl]-piperazin-1-yl}-ethanone | [M + H]$^+$ = 345, 100% @ rt = 3.51 min |
| 6-(3-Chloro-phenyl)-pyrimidine-4-carboxylic acid ((R)-2-hydroxy-propyl)-amide | [M + H]$^+$ = 292, 100% @ rt = 3.77 min |
| 6-(3-Chloro-phenyl)-pyrimidine-4-carboxylic acid (2-methoxy-phenyl)-amide | [M + H]$^+$ = 340, 100% @ rt = 5.45 min |
| 6-(3-Chloro-phenyl)-pyrimidine-4-carboxylic acid (4-methoxy-phenyl)-amide | [M + H]$^+$ = 339, 100% @ rt = 5.43 min |
| 6-(3-Chloro-phenyl)-pyrimidine-4-carboxylic acid (3-methoxy-phenyl)-amide | [M + H]$^+$ = 340, 100% @ rt = 5.16 min |
| Sodium; 6-(3-chloro-phenyl)-pyrimidine-4-sulfonate | [M + H]$^+$ = 271, 96.9% @ rt = 3.13 min |
| 6-m-Tolyl-pyrimidine-4-carboxylic acid | [M + H]$^+$ = 215, 100% @ rt = 3.90 min |
| 6-(3-Chloro-phenyl)-pyrimidine-4-carboxylic acid methyl-phenyl-amide | [M + H]$^+$ = 324, 100% @ rt = 4.48 min |
| [6-(3,4-Dichloro-phenyl)-pyrimidin-4-yl]-(2,3-dihydro-indol-1-yl)-methanone | [M + H]$^+$ = 369, 100% @ rt = 5.38 min |
| N-[6-(3-Chloro-phenyl)-pyrimidine-4-carbonyl]-methanesulfonamide | [M + H]$^+$ = 311/313, 100% @ rt = 4.08 min |
| 6-(3-Chloro-phenyl)-pyrimidine-4-carboxylic acid pyridin-2-ylamide | [M + H]$^+$ = 310, 100% @ rt = 4.98 min |
| 6-(3-Chloro-phenyl)-pyrimidine-4-carboxylic acid pyridin-4-ylamide | [M + H]$^+$ = 310, 100% @ rt = 3.08 min |
| 6-(3-Chloro-phenyl)-pyrimidine-4-carboxylic acid (pyridin-4-ylmethyl)-amide | [M + H]$^+$ = 324, 97% @ rt = 2.98 min |
| [6-(3-Chloro-phenyl)-pyrimidin-4-yl]-(4-methyl-piperidin-1-yl)-methanone | [M + H]$^+$ = 316, 97% @ rt = 4.64 min |
| [6-(3-Chloro-phenyl)-pyrimidin-4-yl]-((R)-3-hydroxy-pyrrolidin-1-yl)-methanone | [M + H]$^+$ = 304, 100% @ rt = 3.48 min |
| 6-(3-Chloro-phenyl)-pyrimidine-4-carboxylic acid [1,3,4]thiadiazol-2-ylamide | [M + H]$^+$ = 317, 100% @ rt = 4.18 min |
| 6-(3-Chloro-phenyl)-pyrimidine-4-carboxylic acid isoxazol-3-ylamide | [M + H]$^+$ = 300, 93% @ rt = 4.48 min |

-continued

| IUPAC name | Mass Spec Result |
|---|---|
| 6-(3-Chloro-phenyl)-pyrimidine-4-carboxylic acid ((R)-1-phenyl-ethyl)-amide | $[M + H]^+$ = 338, 100% @ rt = 5.11 min |
| 6-(3-Chloro-phenyl)-pyrimidine-4-carboxylic acid ((S)-1-phenyl-ethyl)-amide | $[M + H]^+$ = 338, 100% @ rt = 5.10 min |
| [6-(3-Chloro-phenyl)-pyrimidin-4-yl]-((S)-3-hydroxy-pyrrolidin-1-yl)-methanone | $[M + H]^+$ = 304, 100% @ rt = 3.48 min |
| 6-(3-Chloro-phenyl)-pyrimidine-4-carboxylicacid[4-(4-methyl-piperazin-1-yl)-phenyl]-amide | $[M + H]^+$ = 408, 99% @ rt = 3.30 min |
| 6-(3-Chloro-phenyl)-pyrimidine-4-carboxylic acid (6-trifluoromethyl-pyridin-3-yl)-amide | $[M + H]^+$ = 378, 100% @ rt = 5.13 min |
| 6-(3-Chloro-phenyl)-pyrimidine-4-carboxylic acid (pyridin-3-ylmethyl)-amide | $[M + H]^+$ = 324, 100% @ rt = 3.15 min |
| 6-(3-Chloro-phenyl)-pyrimidine-4-carboxylic acid pyridazin-3-ylamide | $[M + H]^+$ = 311, 100% @ rt = 4.36 min |
| 6-(3-Chloro-phenyl)-pyrimidine-4-carboxylic acid pyrazin-2-ylamide | $[M + H]^+$ = 311, 98% @ rt = 4.67 min |
| 6-(3-Chloro-phenyl)-pyrimidine-4-carboxylic acid (4-morpholin-4-yl-phenyl)-amide | $[M + H]^+$ = 395, 100% @ rt = 4.91 min |
| (S)-1-[6-(3-Chloro-phenyl)-pyrimidine-4-carbonyl]-pyrrolidine-2-carboxylic acid amide | $[M + H]^+$ = 331, 100% @ rt = 3.39 min |
| (R)-1-[6-(3-Chloro-phenyl)-pyrimidine-4-carbonyl]-pyrrolidine-2-carboxylic acid amide | $[M + H]^+$ = 331, 99% @ rt = 3.41 min |
| Azetidin-1-yl-[6-(3-chloro-phenyl)-pyrimidin-4-yl]-methanone | $[M + H]^+$ = 273, 100% @ rt = 4.25 min |
| 6-(4-Methoxy-phenyl)-pyrimidine-4-carboxylic acid | $[M + H]^+$ = 231, 100% @ rt = 3.52 min |
| [6-(3-Chloro-phenyl)-pyrimidin-4-yl]-(1,3-dihydro-isoindol-2-yl)-methanone | $[M + H]^+$ = 335, 100% @ rt = 5.32 min |
| [6-(3,4-Dichloro-phenyl)-pyrimidin-4-yl]-(3,4-dihydro-2H-quinolin-1-yl)-methanone | $[M + H]^+$ = 384, 100% @ rt = 5.13 min |
| 6-(3,4-Dichloro-phenyl)-pyrimidine-4-carboxylic acid phenylamide | $[M + H]^+$ = 344, 100% @ rt = 5.41 min |
| 6-(3,4-Dichloro-phenyl)-pyrimidine-4-carboxylic acid p-tolylamide | $[M + H]^+$ = 358, 100% @ rt = 5.61 min |
| 6-(3,4-Dichloro-phenyl)-pyrimidine-4-carboxylic acid (5-methoxy-pyridin-3-yl)-amide | $[M + H]^+$ = 374, 100% @ rt = 4.67 min |
| 6-(3,4-Dichloro-phenyl)-pyrimidine-4-carboxylic acid pyrimidin-5-ylamide | $[M + H]^+$ = 346, 100% @ rt = 4.47 min |
| 6-(3,4-Dichloro-phenyl)-pyrimidine-4-carboxylic acid (6-methyl-pyridin-3-yl)-amide | $[M + H]^+$ = 360, 100% @ rt = 3.82 min |
| 6-(3,4-Dichloro-phenyl)-pyrimidine-4-carboxylic acid (6-methyl-pyridin-3-yl)-amide hydrochloride salt | $[M + H]^+$ = 358, 100% @ rt = 3.76 min |
| 6-(3,4-Dichloro-phenyl)-pyrimidine-4-carboxylic acid (2-methyl-pyridin-3-yl)-amide | $[M + H]^+$ = 360, 100% @ rt = 4.09 min |
| 6-(3-Chloro-phenyl)-pyrimidine-4-carboxylic acid pyrimidin-2-ylamide | $[M + H]^+$ = 312, 100% @ rt = 4.12 min |
| 6-(3-Chloro-phenyl)-pyrimidine-4-carboxylic acid methyl-p-tolyl-amide | $[M + H]^+$ = 338, 100% @ rt = 4.68 min |
| 6-(3-Fluoro-phenyl)-pyrimidine-4-carboxylic acid methyl ester | $[M + H]^+$ = 232, 100% @ rt = 3.87 min |
| 6-(3-Chloro-phenyl)-pyrimidine-4-carboxylic acid (6-methyl-pyridin-3-yl)-amide | $[M + H]^+$ = 325, 100% @ rt = 3.39 min |
| 6-(3-Chloro-phenyl)-pyrimidine-4-carboxylic acid (2-methyl-pyridin-3-yl)-amide | $[M + H]^+$ = 325, 100% @ rt = 3.63 min |
| 6-(3-Chloro-phenyl)-pyrimidine-4-carboxylic acid (4-fluoro-phenyl)-amide | $[M + H]^+$ = 327, 100% @ rt = 5.25 min |
| 6-(3-Fluoro-phenyl)-pyrimidine-4-carboxylic acid | $[M + H]^+$ = 219, 100% @ rt = 3.54 min |
| 6-(3,5-Dichloro-phenyl)-pyrimidine-4-carboxylic acid phenylamide | $[M + H]^+$ = 344, 100% @ rt = 5.47 min |
| [6-(3,5-Dichloro-phenyl)-pyrimidin-4-yl]-(2,3-dihydro-indol-1-yl)-methanone | $[M + H]^+$ = 369, 100% @ rt = 5.38 min |
| 6-(3,5-Dichloro-phenyl)-pyrimidine-4-carboxylic acid p-tolylamide | $[M + H]^+$ = 358, 100% @ rt = 5.67 min |
| 6-(3,5-Dichloro-phenyl)-pyrimidine-4-carboxylic acid (5-methoxy-pyridin-3-yl)-amide | $[M + H]^+$ = 375, 100% @ rt = 4.75 min |

-continued

| IUPAC name | Mass Spec Result |
| --- | --- |
| 6-(3-Chloro-phenyl)-pyrimidine-4-carboxylic acid (1-methyl-1H-pyrazol-3-yl)-amide | $[M + H]^+$ = 314, 100% @ rt = 4.39 min |
| 6-(3-Chloro-phenyl)-pyrimidine-4-carboxylic acid (1-methyl-1H-pyrazol-4-yl)-amide | $[M + H]^+$ = 313, 99% @ rt = 4.15 min |
| 6-(3-Chloro-phenyl)-pyrimidine-4-carboxylic acid (4-methoxy-phenyl)-methyl-amide | $[M + H]^+$ = 354, 100% @ rt = 4.52 min |
| [6-(3-Chloro-phenyl)-pyrimidin-4-yl]-(2-methyl-2,3-dihydro-indol-1-yl)-methanone | $[M + H]^+$ = 349, 100% @ rt = 5.28 min |
| 6-(3-Fluoro-phenyl)-pyrimidine-4-carboxylic acid pyridin-3-ylamide | $[M + H]^+$ = 294, 100% @ rt = 3.61 min |
| 6-(3-Chloro-phenyl)-pyrimidine-4-carboxylic acid (2,2-difluoro-benzo[1,3]dioxol-5-yl)-amide | $[M + H]^+$ = 389, 100% @ rt = 5.43 min |
| [6-(3-Chloro-phenyl)-pyrimidin-4-yl]-(5-fluoro-2,3-dihydro-indol-1-yl)-methanone | $[M + H]^+$ = 354, 100% @ rt = 5.04 min |
| (5-Chloro-2,3-dihydro-indol-1-yl)-[6-(3-chloro-phenyl)-pyrimidin-4-yl]-methanone | $[M + H]^+$ = 370, 100% @ rt = 5.31 min |
| 6-(3,5-Dichloro-phenyl)-pyrimidine-4-carboxylic acid pyrimidin-5-ylamide | $[M + H]^+$ = 345, 97% @ rt = 4.56 min |
| 6-(3-Chloro-4-trifluoromethyl-phenyl)-pyrimidine-4-carboxylic acid methyl ester | $[M + H]^+$ = 316, 99% @ rt = 4.62 min |
| 6-(3-Chloro-4-trifluoromethyl-phenyl)-pyrimidine-4-carboxylic acid | $[M + H]^+$ = 302, 100% @ rt = 4.38 min |
| 6-(3-Chloro-4-trifluoromethyl-phenyl)-pyrimidine-4-carboxylic acid pyridin-3-ylamide | $[M + H]^+$ = 379, 100% @ rt = 4.34 min |
| [6-(3-Chloro-phenyl)-pyrimidin-4-yl]-(2,3-dihydro-pyrrolo[3,2-c]pyridin-1-yl)-methanone | $[M + H]^+$ = 337, 100% @ rt = 3.24 min |
| 6-(3-Chloro-phenyl)-pyrimidine-4-carboxylic acid (2,2-difluoro-benzo[1,3]dioxol-5-yl)-methyl-amide | $[M + H]^+$ = 403, 100% @ rt = 4.85 min |
| 6-(3-Chloro-phenyl)-pyrimidine-4-carboxylic acid thiazol-2-ylamide | $[M + H]^+$ = 316, 100% @ rt = 4.75 min |
| 6-(3-Chloro-phenyl)-pyrimidine-4-carboxylic acid (3-methyl-isoxazol-5-yl)-amide | $[M + H]^+$ = 314/316, 100% @ rt = 4.69 min |
| 6-(3-Chloro-phenyl)-pyrimidine-4-carboxylic acid (5-methyl-[1,3,4]oxadiazol-2-yl)-amide | $[M + H]^+$ = 315/317, 100% @ rt = 3.92 min |
| 6-(3-Chloro-phenyl)-pyrimidine-4-carboxylic acid oxazol-2-ylamide | $[M + H]^+$ = 300/302, 100% @ rt = 4.08 min |
| 6-(3-Chloro-phenyl)-pyrimidine-4-carboxylic acid (3-methyl-[1,2,4]thiadiazol-5-yl)-amide | $[M + H]^+$ = 331, 99% @ rt = 4.59 min |
| 6-(3-Chloro-phenyl)-pyrimidine-4-carboxylic acid (4H-[1,2,4]triazol-3-yl)-amide | LCMS not obtained |
| 6-(3,4-Difluoro-phenyl)-pyrimidine-4-carboxylic acid methyl ester | $[M + H]^+$ = 251, 100% @ rt = 4.11 min |
| 6-(5-Chloro-2-fluoro-phenyl)-pyrimidine-4-carboxylic acid methyl ester | $[M + H]^+$ = 267, 100% @ rt = 4.31 min |
| 6-(3,4-Difluoro-phenyl)-pyrimidine-4-carboxylic acid | $[M + H]^+$ = 236, 100% @ rt = 3.74 min |
| 6-(3,4-Difluoro-phenyl)-pyrimidine-4-carboxylic acid pyrimidin-5-ylamide | $[M + H]^+$ = 314, 98% @ rt = 4.09 min |
| 6-(5-Chloro-2-fluoro-phenyl)-pyrimidine-4-carboxylic acid | $[M + H]^+$ = 253, 100% @ rt = 3.64-3.93 min |
| [6-(3,4-Dichloro-phenyl)-pyrimidin-4-yl]-(1',2'-dihydro-spiro[cyclopropane-1,3'-[3H]indol]-1')-methanone | $[M + H]^+$ = 395, 100% @ rt = 5.69 min |
| 6-(3,4-Dichloro-phenyl)-pyrimidine-4-carboxylic acid (2,6-dimethyl-pyridin-3-yl)-amide | $[M + H]^+$ = 374, 100% @ rt = 3.69 min |
| 6-(3,4-Dichloro-phenyl)-pyrimidine-4-carboxylic acid (2,6-dimethyl-pyridin-3-yl)-amide hydrochloride salt | $[M + H]^+$ = 372, 100% @ rt = 3.56 min |
| 6-(3,4-Dichloro-phenyl)-pyrimidine-4-carboxylic acid (3-methyl-isoxazol-5-yl)-amide | $[M + H]^+$ = 348, 100% @ rt = 5.13 min |
| 6-(3-Chloro-4-fluoro-phenyl)-pyrimidine-4-carboxylic acid methyl ester | $[M + H]^+$ = 266, 100% @ rt = 4.35 min |
| 6-(3,4-Dichloro-phenyl)-pyrimidine-4-carboxylic acid (5-methy-[1,3,4]oxadiazol-2-yl)-amide | $[M + H]^+$ = 350, 99% @ rt = 4.19 min |

| IUPAC name | Mass Spec Result |
|---|---|
| 6-(3-Chloro-4-methoxy-phenyl)-pyrimidine-4-carboxylic acid methyl ester | [M + H]⁺ = 279, 100% @ rt = 4.35 min |
| 6-(3-Chloro-4-methoxy-phenyl)-pyrimidine-4-carboxylic acid | [M + H]⁺ = 264, 100% @ rt = 3.73-4.10 min |
| 6-(3,4-Dichloro-phenyl)-pyrimidine-4-carboxylic acid (pyridin-4-ylmethyl)-amide | [M + H]⁺ = 360, 100% @ rt = 3.46 min |
| 6-(3-Chloro-4-fluoro-phenyl)-pyrimidine-4-carboxylic acid | [M + H]⁺ = 292, 100% @ rt = 3.92-4.23 min |
| 6-(3,4-Dichloro-phenyl)-pyrimidine-4-carboxylic acid [1,3,4]thiadiazol-2-ylamide | [M + H]⁺ = 351, 100% @ rt = 4.42 min |
| 6-(3,4-Dichloro-phenyl)-pyrimidine-4-carboxylic acid (2-amino-ethyl)-amide | [M + H]⁺ = 312, 96% @ rt = 3.18 min |
| (5-Chloro-2,3-dihydro-indol-1-yl)-[6-(3,4-dichloro-phenyl)-pyrimidin-4-yl]-methanone | [M + H]⁺ = 405, 100% @ rt = 5.44 min |
| [6-(3,4-Dichloro-phenyl)-pyrimidin-4-yl]-(5-fluoro-2,3-dihydro-indol-1-yl)-methanone | [M + H]⁺ = 387, 100% @ rt = 5.46 min |
| [6-(3,4-Dichloro-phenyl)-pyrimidin-4-yl]-(5-morpholin-4-yl-2,3-dihydro-indol-1-yl)-methanone | [M + H]⁺ = 455, 100% @ rt = 5.17 min |
| 6-(3,4-Dichloro-phenyl)-5-fluoro-pyrimidine-4-carboxylic acid | [M + H]⁺ = 286, 100% @ rt = 3.85 min |
| 6-(3,4-Dichloro-phenyl)-pyrimidine-4-carboxylic acid pyridin-4-ylamide | [M + H]⁺ = 346, 100% @ rt = 3.33 min |
| 6-(3,4-Dichloro-phenyl)-pyrimidine-4-carboxylic acid pyridin-2-ylamide | [M + H]⁺ = 344, 100% @ rt = 5.19 min |
| 6-(3,4-Dichloro-phenyl)-pyrimidine-4-carboxylic acid (1-methyl-1H-pyrazol-4-yl)-amide | [M + H]⁺ = 347, 98% @ rt = 4.40 min |
| 6-(3,4-Dichloro-phenyl)-pyrimidine-4-carboxylic acid isoxazol-3-ylamide | [M + H]⁺ = 334, 100% @ rt = 4.68 min |
| 6-(3,4-Dichloro-phenyl)-pyrimidine-4-carboxylic acid thiazol-2-ylamide | [M + H]⁺ = 350, 100% @ rt = 4.87 min |
| [6-(3,4-Dichloro-phenyl)-pyrimidin-4-yl]-(1,3-dihydro-isoindol-2-yl)-methanone | [M + H]⁺ = 369, 100% @ rt = 5.25 min |
| 6-(3,4-Dichloro-phenyl)-pyrimidine-4-carboxylic acid (4H-[1,2,4]triazol-3-yl)-amide | LCMS not obtained |
| 4-(3,4-Dichloro-phenyl)-6-(5-fluoro-pyridin-2-yl)-pyrimidine | [M + H]⁺ = 319, 100% @ rt = 5.41 min |
| 6-(3,4-Difluoro-phenyl)-pyrimidine-4-carboxylic acid pyridin-3-ylamide | [M + H]⁺ = 313, 100% @ rt = 3.82 min |
| 6-(3-Trifluoromethyl-phenyl)-pyrimidine-4-carboxylic acid pyrimidin-5-ylamide | [M + H]⁺ = 345, 100% @ rt = 4.23 min |
| 6-(3,4-Dichloro-phenyl)-pyrimidine-4-carboxylic acid (2-methyl-pyrimidin-5-yl)-amide | [M + H]⁺ = 359, 100% @ rt = 4.47 min |
| 6-(3-Chloro-4-methyl-phenyl)-pyrimidine-4-carboxylic acid methyl ester | [M + H]⁺ = 263, 99.8% @ rt = 4.36 min |
| 6-(3-Chloro-4-methyl-phenyl)-pyrimidine-4-carboxylic acid | [M + H]⁺ = 248, 100% @ rt = 4.21 min |
| 6-(3-Chloro-4-fluoro-phenyl)-pyrimidine-4-carboxylic acid pyridin-3-ylamide | [M + H]⁺ = 328, 100% @ rt = 3.96 min |
| 6-(3-Chloro-4-fluoro-phenyl)-pyrimidine-4-carboxylic acid (2,6-dimethyl-pyridin-3-yl)-amide | [M + H]⁺ = 358, 100% @ rt = 3.27 min |
| 6-(3,4-Dichloro-phenyl)-pyrimidine-4-carboxylic acid (2-acetylamino-ethyl)-amide | [M + H]⁺ = 354, 100% @ rt = 3.83 min |
| 6-(3,4-Dichloro-phenyl)-pyrimidine-4-sulfonate sodium salt | [M + H]⁺ = 304, 99% @ rt = 3.88 min |
| [6-(3,4-Dichloro-phenyl)-pyrimidin-4-yl]-(3,3-dimethyl-2,3-dihydro-indol-1-yl)-methanone | [M + H]⁺ = 398, 100% @ rt = 5.45 min |
| [6-(3,4-Dichloro-phenyl)-pyrimidin-4-yl]-(4-hydroxy-piperidin-1-yl)-methanone | [M + H]⁺ = 352, 100% @ rt = 3.88 min |
| [6-(3,4-Dichloro-phenyl)-pyrimidin-4-yl]-morpholin-4-yl-methanone | [M + H]⁺ = 337, 100% @ rt = 4.21 min |
| 6-(3-Chloro-4-fluoro-phenyl)-pyrimidine-4-carboxylic acid pyrimidin-5-ylamide | [M + H]⁺ = 329, 100% @ rt = 4.21 min |
| 6-(3,4-Dichloro-phenyl)-5-fluoro-pyrimidine-4-carboxylic acid methyl ester | [M + H]⁺ = 302, 98% @ rt = 4.63 min |
| 6-(3,4-Dichloro-phenyl)-5-fluoro-pyrimidine-4-carboxylic acid | [M + H]⁺ = 286, 100% @ rt = 3.85 min |
| 6-(3,4-Dichloro-phenyl)-5-fluoro-pyrimidine-4-carboxylic acid pyridin-3-ylamide | [M + H]⁺ = 362, 99% @ rt = 4.07 min |

-continued

| IUPAC name | Mass Spec Result |
| --- | --- |
| 6-(3,4-Dichloro-phenyl)-5-fluoro-pyrimidine-4-carboxylic acid (2,6-dimethyl-pyridin-3-yl)-amide | $[M + H]^+$ = 391, 98% @ rt = 3.51 min |
| 6-(3,4-Dichloro-phenyl)-5-fluoro-pyrimidine-4-carboxylic acid pyrimidin-5-ylamide | $[M + H]^+$ = 363, 100% @ rt = 4.34 min |
| 2-(3-Chloro-phenyl)-isonicotinic acid methyl ester | $[M + H]^+$ = 248, 95% @ rt = 4.52 min |
| 2-(3-Chloro-phenyl)-isonicotinic acid hydrochloride salt | $[M + H]^+$ = 234/236, 100% @ rt = 3.95 min |
| 4-(3-Chloro-phenyl)-pyridine-2-carboxylic acid | $[M + H]^+$ = 234/530, 95% @ rt = 4.26 min |
| 4-(3-Chloro-phenyl)-pyridine-2-carboxylic acid methyl ester | $[M + H]^+$ = 248, 98% @ rt = 4.50 min |
| 4-(3-Chloro-phenyl)-pyridine-2-carboxylic acid pyridin-3-ylamide | $[M + H]^+$ = 310, 100% @ rt = 4.12 min |
| 4-(3-Chloro-phenyl)-pyridine-2-carboxylic acid phenylamide | $[M + H]^+$ = 309, 100% @ rt = 5.15 min |
| [4-(3-Chloro-phenyl)-pyridin-2-yl]-(2,3-dihydro-indol-1-yl)-methanone | $[M + H]^+$ = 335, 100% @ rt = 4.91 min |
| 4-(3-Chloro-phenyl)-pyridine-2-carboxylic acid p-tolylamide | $[M + H]^+$ = 323, 100% @ rt = 5.37 min |
| 4-(3-Chloro-phenyl)-pyridine-2-carboxylic acid (5-methoxy-pyridin-3-yl)-amide | $[M + H]^+$ = 340, 99% @ rt = 4.32 min |
| 4-(3,5-Dichloro-phenyl)-pyridine-2-carboxylic acid phenylamide | $[M + H]^+$ = 343, 100% @ rt = 5.47 min |
| 4-(3,5-Dichloro-phenyl)-pyridine-2-carboxylic acid p-tolylamide | $[M + H]^+$ = 357, 100% @ rt = 5.65 min |
| 4-(3,5-Dichloro-phenyl)-pyridine-2-carboxylic acid pyridin-3-ylamide | $[M + H]^+$ = 345, 100% @ rt = 4.21 min |
| 4-(3,5-Dichloro-phenyl)-pyridine-2-carboxylic acid (5-methoxy-pyridin-3-yl)-amide | $[M + H]^+$ = 375, 100% @ rt = 4.72 min |
| [4-(3,5-Dichloro-phenyl)-pyridin-2-yl]-(2,3-dihydro-indol-1-yl)-methanone | $[M + H]^+$ = 368, 100% @ rt = 5.42 min |
| 4-(3-Chloro-phenyl)-pyridine-2-carboxylic acid pyrimidin-5-ylamide | $[M + H]^+$ = 310, 100% @ rt = 4.23 min |
| 4-(3,4-Dichloro-phenyl)-pyridine-2-carboxylic acid phenylamide | $[M + H]^+$ = 342, 100% @ rt = 5.40 min |
| 4-(3,4-Dichloro-phenyl)-pyridine-2-carboxylic acid p-tolylamide | $[M + H]^+$ = 357, 100% @ rt = 5.59 min |
| 4-(3,4-Dichloro-phenyl)-pyridine-2-carboxylic acid pyridin-3-ylamide | $[M + H]^+$ = 344, 98% @ rt = 4.13 min |
| [4-(3,4-Dichloro-phenyl)-pyridin-2-yl]-(2,3-dihydro-indol-1-yl)-methanone | $[M + H]^+$ = 369, 100% @ rt = 5.14 min |
| 4-(3,4-Dichloro-phenyl)-pyridine-2-carboxylic acid (5-methoxy-pyridin-3-yl)-amide | $[M + H]^+$ = 374, 375.7, 100% @ rt = 4.66 min |
| 4-(3,4-Dichloro-phenyl)-pyridine-2-carboxylic acid hydrochloride salt | $[M + H]^+$ = 268, 98% @ rt = 4.26 min |
| 4-(3,4-Dichloro-phenyl)-pyridine-2-carboxylic acid pyrimidin-5-ylamide | $[M + H]^+$ = 344, 100% @ rt = 4.56 min |
| 4-(3,5-Dichloro-phenyl)-pyridine-2-carboxylic acid hydrocloride salt | $[M + H]^+$ not observed; poor ionisation |
| 4-(3,5-Dichloro-phenyl)-pyridine-2-carboxylic acid pyrimidin-5-ylamide | $[M + H]^+$ = 344, 100% @ rt = 4.67 min |
| 5-Morpholin-4-yl-pyridine-2-carboxylic acid tert-butyl ester | $[M + H]^+$ = 265, 98% @ rt = 3.50 min |

Example 12

A generalized procedure for monitoring L-Kynurenine (KYN) hydroxylation to form product 3-Hydroxy-Kynurenine (3OH-KYN) by LC/MS is described below. Product is quantified by multiple reaction monitoring using MS.

Key Reagents:
Compound: Stock concentrations: 10 mM in 100% DMSO
Cell line: CHO GST HIS KMO cell line, 1E4 cells/well/100 µl in 96 well cell plate
Substrate: L-Kynurenine (Sigma: Cat# K3750, stock concentration: 10 mM in 100 mM potassium phosphate buffer, pH 7.4)

Assay Conditions:
Medium: OptiMem (Reduced Serum Medium 1×, +L-Glutamine+HEPES−Phenol Red; GIBCO: Cat#11058)
Assay Volume: 200 µl
Plate Format: 96 well plate, transparent (Corning)
Read-Out: product (3OH-KYN) quantification using product specific MRM
Reader: LC/MS/MS
Assay Protocol:
prepare serial dilution (factor 3) of compound in 100% DMSO (top concentration=6.67 mM, 100% DMSO)

[8 points: 6.67 mM; 2.22 mM; 0.74 mM; 0.247 mM; 0.082 mM; 0.027 mM; 0.009 mM; 0.003 mM]
prepare 300-fold concentrated solution of each compound concentration (top concentration 22.22 μM, 0.3% DMSO) in OptiMem medium
[22.2 μM; 7.41 μM; 2.47 μM; 0.82 μM; 0.27 μM; 0.09 μM; 0.03 μM; 0.01 μM]
prepare substrate (10 mM) at concentration of 1.1 mM in medium
medium of cell plate is drawed off
cells are washed with OptiMem (100 μl/well) and drawed off again
assay mix: 90 μl OptiMem/well+900 compound/well of each concentration
[final compound top concentration: 10 μM; 0.15% DMSO]
[final compound bottom concentration: 0.004 μM; 0.15% DMSO]
pre-incubation: 30 min at 37° C.
add 20 μl/well of the 1.1 mM substrate solution (final assay concentration: 100 μM)
positive control: 200 μl OptiMem
negative control: 180 μl OptiMem+20 μl mM substrate
incubate ~24 h at 37° C.
transfer 100 μl of each well in a transparent 96 well plate (Corning)
add 100 μl/well 10% trichloro acetic acid (TCA) in water
centrifugate plate for 3 min at 4000 rpm
detect product by LC/MS (injection of 50 μl/well; 2.5 fold overfill of the 20 μl sample loop)

Data Analysis:
$IC_{50}$'s are calculated using automated fitting algorithm (A+Analysis).

Example 13

A method of monitoring L-Kynurenine (KYN) hydroxylation to form product 3-Hydroxy-Kynurenine (3OH-KYN) by LC/MS is described below. Product is quantified by multiple reaction monitoring.
Key Reagents:
Compound: Stock concentrations: 10 mM in 100% DMSO
Enzyme: KMO enzyme prepared at Evotec via mitochondria isolation from CHO-GST HIS KMO cells
Substrate: L-Kynurenine (Sigma: Cat# K3750) [stock concentration: 10 mM in 100 mM potassium phosphate buffer, pH 7.4]
Assay Conditions:
Buffer: 100 mM potassium phosphate, pH 7.4, 20 μM NADPH, 0.4 U/ml G6P-DH (Glucose 6-phosphate dehydrogenase), 3 mM G6P (D-Glucose 6-phosphate)
Assay Volume: 40 μl
Plate Format: 384 well plate, transparent (Matrix)
Read-Out: product (3OH-KYN) quantification using product specific MRM
Reader: LC/MS/MS
Assay Protocol:
prepare serial dilution (factor 3) of compound in 100% DMSO (top concentration=10 mM, 100% DMSO)
[8 points: 10 mM; 3.33 mM; 1.11 mM; 0.37 mM; 0.12 mM; 0.04 mM; 0.0137 mM; 0.0045 mM, 0.0015 mM]
prepare 3.33-fold concentrated solution of each compound concentration (top concentration 300 μM, 3% DMSO) in assay buffer
[concentrations: 300 μM; 100 μM; 33.3 μM; 11.1 μM; 3.70 μM; 1.23 μM; 0.41 μM; 0.137 μM]
prepare substrate (10 mM) at concentration of 1 mM in assay buffer
assay mix: 4 μl compound/well of each concentration+24 μl assay buffer/well+8 μl KMO human enzyme+4 μl mM substrate (final concentration=100 μM) [final compound top concentration: 3 μM; 0.3% DMSO]
[final compound bottom concentration: 0.0137 μM; 0.3% DMSO]
positive control: 4 μl 50 μM FCE28833 in assay buffer [0.5% DMSO] (final assay concentration=5 μM)+24 μl assay buffer/well+8 μl KMO human enzyme+4 μl 1 mM substrate (final concentration=10 μM)
negative control: 28 μl assay buffer/well+8 μl KMO human enzyme+4 μl 1 mM substrate (final concentration=10 μM)
incubate 400 min at RT
add 40 μl/well 10% trichloro acetic acid in water to stop the assay and precipitate protein
centrifuge plate for 3 min at 4000 rpm
product detection by LC/MS (injection of 50 μl/well; 2.5 fold overfill of the 20 μl sample loop)

Data Analysis:
$IC_{50}$'s are calculated using automated fitting algorithm (A+Analysis).

Example 14

A method of monitoring L-Kynurenine (KYN) hydroxylation to form 3-Hydroxy-Kynurenine (3OH-KYN) by LC/MS is described. Product is quantified by multiple reaction monitoring (MRM method).
Key Reagents:
Compound: Stock concentrations: 10 mM in 100% DMSO
Enzyme: KMO enzyme prepared at Evotec from mouse liver (4-6 weeks old) via mitochondria isolation as described in the literature
Substrate: L-Kynurenine (Sigma: Cat# K3750, stock concentration: 10 mM in 100 mM potassium phosphate buffer, pH 7.4)
Assay Conditions:
Buffer: 100 mM potassium phosphate, pH 7.4, 20 μM NADPH, 0.4 U/ml G6P-DH (Glucose 6-phosphate Dehydrogenase), 3 mM G6P (D-Glucose 6-phosphate)
Assay Volume: 40 μl
Plate Format: 384 well plate, transparent (Matrix)
Read-Out: product (3OH-KYN) quantification using product specific MRM
Reader: LC/MS/MS
Assay Protocol:
prepare serial dilution (factor 3) of compound in 100% DMSO (top concentration=10 mM, 100% DMSO)
[8 points: 10 mM; 3.33 mM; 1.11 mM; 0.37 mM; 0.12 mM; 0.04 mM; 0.0137 mM; 0.0045 mM, 0.0015 mM]
prepare 3.33-fold concentrated solution of each compound concentration (top concentration 300 μM, 3% DMSO) in assay buffer
[concentrations: 300 μM; 100 μM; 33.3 μM; 11.1 μM; 3.70 μM; 1.23 μM; 0.41 μM; 0.137 μM]
prepare substrate (10 mM) at concentration of 1 mM in assay buffer
assay mix: 4 μl compound/well of each concentration+24 μl assaybuffer/well+8 μl KMO mouse enzyme+4 μl 1 mM substrate (final concentration=10 μM) [final compound top concentration: 30 μM; 0.3% DMSO]
[final compound bottom concentration: 0.0137 μM; 0.3% DMSO]
positive control: 4 μl 50 μM FCE28833 in assay buffer, 0.5% DMSO [final assay concentration=5 μM]+24 μl assaybuffer/well+8 μl KMO mouse enzyme+4 μl 1 mM substrate [final concentration=10 μM]

negative control: 28 μl assay buffer/well+8 μl KMO mouse enzyme+4 μl 1 mM substrate [final concentration=10 μM]

incubate 40 min at RT add 40 μl/well 10% trichloro acetic acid in water to stop the assay and precipitate protein centrifuge plate for 3 min at 4000 rpm product detection by LC/MS (injection of 20 μl/well, 2 fold overfill of the 10 μl sample loop)

Data Analysis:

$IC_{50}$'s are calculated using automated fitting algorithm (A+Analysis).

Example 15

Using procedures similar to those described herein, the following compounds were assayed for activity.

| IUPAC name | INH.Mouse @ 10 μM |
|---|---|
| 6-(3,4-Dichloro-phenyl)-pyrimidine-4-carboxylic acid methyl ester | 101.4 |
| 6-(3-Chloro-phenyl)-pyrimidine-4-carboxylic acid methyl ester | 105.6 |
| 6-(3,5-Dichloro-phenyl)-pyrimidine-4-carboxylic acid methyl ester | 101.2 |
| 6-(3,4-Dichloro-phenyl)-2-methyl-pyrimidine-4-carboxylic acid methyl ester | 95.5 |
| 6-(3,4-Dichloro-phenyl)-pyrimidine-4-carboxylic acid | 105.5 |
| 6-(3-Chloro-phenyl)-pyrimidine-4-carboxylic acid | 105.6 |
| 6-(3,5-Dichloro-phenyl)-pyrimidine-4-carboxylic acid | 102.1 |
| 6-(3,4-Dichloro-phenyl)-2-methyl-pyrimidine-4-carboxylic acid | 102.5 |
| 6-(3,4-Dichloro-phenyl)-pyrimidine-4-carboxylic acid pyridin-3-ylamide | 83.5 |
| 6-(3-Chloro-phenyl)-pyrimidine-4-carboxylic acid pyridin-3-ylamide | 98.6 |
| N-[6-(3,4-Dichloro-phenyl)-pyrimidin-4-yl]-3,4-dimethoxy-benzenesulfonamide | 85.0 |
| N-[6-(3,4-Dichloro-phenyl)-pyrimidin-4-yl]-methanesulfonamide | 51.2 |
| 6-(3-chloro-phenyl)-pyrimidine-4-carboxylic acid sodium salt | 100.0 |
| 6-(3-Chloro-phenyl)-pyrimidine-4-carboxylic acid cyclohexyl ammonium salt | 100.0 |
| 6-(3,4-dichloro-phenyl)-pyrimidine-4-carboxylic acid sodium salt | 100.0 |
| 6-(3-Chloro-phenyl)-pyrimidine-4-carboxylic acid pyrimidin-5-ylamide | 100.0 |
| 6-(4-Fluoro-3-trifluoromethyl-phenyl)-pyrimidine-4-carboxylic acid methyl ester | 92.7 |
| 6-(3-Trifluoromethyl-phenyl)-pyrimidine-4-carboxylic acid methyl ester | 94.5 |
| 6-(4-Fluoro-3-trifluoromethyl-phenyl)-pyrimidine-4-carboxylic acid | 94.8 |
| 6-(3,5-Dichloro-phenyl)-pyrimidine-4-carboxylic acid pyridin-3-ylamide | 72.2 |
| 6-(3-Trifluoromethyl-phenyl)-pyrimidine-4-carboxylic acid | 77.7 |
| 6-(3-Chloro-phenyl)-pyrimidine-4-carboxylic acid ethylamide | 100.0 |
| 6-(5-Fluoro-pyridin-3-yl)-pyrimidine-4-carboxylic acid | 96.1 |
| 6-(3-Chloro-phenyl)-pyrimidine-4-carboxylic acid amide | 77.5 |
| 6-(3-Chloro-phenyl)-pyrimidine-4-carboxylic acid methylamide | 100.0 |
| 6-(5-Fluoro-pyridin-3-yl)-pyrimidine-4-carboxylic acid methyl ester | 87.2 |
| 6-(3-Fluoro-5-trifluoromethyl-phenyl)-pyrimidine-4-carboxylic acid | 75.8 |
| 6-(5-Chloro-pyridin-3-yl)-pyrimidine-4-carboxylic acid methyl ester | 93.2 |
| 6-(5-Chloro-pyridin-3-yl)-pyrimidine-4-carboxylic acid | 91.7 |
| 6-(3-Chloro-phenyl)-pyrimidine-4-carboxylic acid isopropylamide | 100.0 |
| [6-(3-Chloro-phenyl)-pyrimidin-4-yl]-morpholin-4-yl-methanone | 100.0 |
| 6-(3-Chloro-phenyl)-pyrimidine-4-carboxylic acid propylamide | 72.4 |
| 6-(3-Chloro-phenyl)-pyrimidine-4-carboxylic acid phenylamide | 100.0 |
| 6-Pyridin-3-yl-pyrimidine-4-carboxylic acid methyl ester trifluoroacetic acid salt | 74.5 |
| 6-Phenyl-pyrimidine-4-carboxylic acid | 100.0 |
| 6-(2-Fluoro-5-trifluoromethyl-phenyl)-pyrimidine-4-carboxylic acid | 80.3 |
| 6-(3-Chloro-phenyl)-pyrimidine-4-carboxylic acid o-tolylamide | 96.2 |
| 6-(3-Chloro-phenyl)-pyrimidine-4-carboxylic acid p-tolylamide | 100.0 |
| [6-(3-Chloro-phenyl)-pyrimidin-4-yl]-(3,4-dihydro-2H-quinolin-1-yl)-methanone | 100.0 |
| Phenyl-pyrimidine-4-carboxylic acid methyl ester | 100.0 |
| 6-(2,4-Difluoro-phenyl)-pyrimidine-4-carboxylic acid methyl ester | 100.0 |
| 6-(2,4-Difluoro-phenyl)-pyrimidine-4-carboxylic acid | 100.0 |
| 6-(3-Chloro-phenyl)-pyrimidine-4-carboxylic acid (6-methoxy-pyridin-3-yl)-amide | 93.4 |
| [6-(3-Chloro-phenyl)-pyrimidin-4-yl]-(2,3-dihydro-indol-1-yl)-methanone | 100.0 |
| 6-(3-Chloro-phenyl)-pyrimidine-4-carboxylic acid m-tolylamide | 96.6 |
| 6-(3-Chloro-phenyl)-pyrimidine-4-carboxylic acid methyl-pyridin-3-yl-amide | 95.2 |
| 6-(3-Chloro-phenyl)-pyrimidine-4-carboxylic acid (5-methoxy-pyridin-3-yl)-amide | 100.0 |
| 6-(3-Chloro-2-fluoro-phenyl)-pyrimidine-4-carboxylic acid methyl ester | 100.0 |
| 6-(3-Chloro-phenyl)-pyrimidine-4-carboxylic acid dimethylamide | 100.0 |
| 6-(3-Chloro-phenyl)-2-methyl-pyrimidine-4-carboxylic acid methyl ester | 100.0 |
| 4-[6-(3-Chloro-phenyl)-pyrimidine-4-carbonyl]-piperazin-2-one | 100.0 |
| 6-(3-Chloro-2-fluoro-phenyl)-pyrimidine-4-carboxylic acid | 100.0 |
| 6-(3-Chloro-phenyl)-pyrimidine-4-carboxylic acid (4-methoxy-pyridin-3-yl)-amide | 91.0 |
| 6-(3-Chloro-phenyl)-2-methyl-pyrimidine-4-carboxylic acid | 100.0 |

-continued

| IUPAC name | INH.Mouse @ 10 µM |
|---|---|
| 6-(3-Chloro-phenyl)-pyrimidine-4-carboxylic acid (2-hydroxy-ethyl)-amide | 95.8 |
| [6-(3-Chloro-phenyl)-pyrimidin-4-yl]-(4-hydroxy-piperidin-1-yl)-methanone | 100.0 |
| 6-(3-Methoxy-phenyl)-pyrimidine-4-carboxylic acid | 81.0 |
| 6-(3-Methoxy-phenyl)-pyrimidine-4-carboxylic acid methyl ester | 77.5 |
| 6-(3-Chloro-phenyl)-pyrimidine-4-carboxylic acid benzylamide | 67.0 |
| [6-(3-Chloro-phenyl)-pyrimidin-4-yl]-(4-methyl-piperazin-1-yl)-methanone | 64.3 |
| [6-(3-Chloro-phenyl)-pyrimidin-4-yl]-pyrrolidin-1-yl-methanone | 90.5 |
| 6-(3-Chloro-phenyl)-pyrimidine-4-carboxylic acid ((S)-2-hydroxy-propyl)-amide | 87.3 |
| 6-m-Tolyl-pyrimidine-4-carboxylic acid methyl ester | 96.3 |
| 1-{4-[6-(3-Chloro-phenyl)-pyrimidine-4-carbonyl]-piperazin-1-yl}-ethanone | 94.9 |
| 6-(3-Chloro-phenyl)-pyrimidine-4-carboxylic acid ((R)-2-hydroxy-propyl)-amide | 74.3 |
| 6-(3-Chloro-phenyl)-pyrimidine-4-carboxylic acid (2-methoxy-phenyl)-amide | 100.0 |
| 6-(3-Chloro-phenyl)-pyrimidine-4-carboxylic acid (4-methoxy-phenyl)-amide | 100.0 |
| 6-(3-Chloro-phenyl)-pyrimidine-4-carboxylic acid (3-methoxy-phenyl)-amide | 97.1 |
| Sodium; 6-(3-chloro-phenyl)-pyrimidine-4-sulfonate | 97.1 |
| 6-m-Tolyl-pyrimidine-4-carboxylic acid | 97.9 |
| 6-(3-Chloro-phenyl)-pyrimidine-4-carboxylic acid methyl-phenyl-amide | 100.0 |
| [6-(3,4-Dichloro-phenyl)-pyrimidin-4-yl]-(2,3-dihydro-indol-1-yl)-methanone | 100.0 |
| N-[6-(3-Chloro-phenyl)-pyrimidine-4-carbonyl]-methanesulfonamide | 99.5 |
| 6-(3-Chloro-phenyl)-pyrimidine-4-carboxylic acid pyridin-2-ylamide | 100.0 |
| 6-(3-Chloro-phenyl)-pyrimidine-4-carboxylic acid pyridin-4-ylamide | 100.0 |
| 6-(3-Chloro-phenyl)-pyrimidine-4-carboxylic acid (pyridin-4-ylmethyl)-amide | 100.0 |
| [6-(3-Chloro-phenyl)-pyrimidin-4-yl]-(4-methyl-piperidin-1-yl)-methanone | 88.2 |
| [6-(3-Chloro-phenyl)-pyrimidin-4-yl]-((R)-3-hydroxy-pyrrolidin-1-yl)-methanone | 83.9 |
| 6-(3-Chloro-phenyl)-pyrimidine-4-carboxylic acid [1,3,4]thiadiazol-2-ylamide | 97.4 |
| 6-(3-Chloro-phenyl)-pyrimidine-4-carboxylic acid isoxazol-3-ylamide | 100.0 |
| 6-(3-Chloro-phenyl)-pyrimidine-4-carboxylic acid ((R)-1-phenyl-ethyl)-amide | 99.2 |
| 6-(3-Chloro-phenyl)-pyrimidine-4-carboxylic acid ((S)-1-phenyl-ethyl)-amide | 99.8 |
| [6-(3-Chloro-phenyl)-pyrimidin-4-yl]-((S)-3-hydroxy-pyrrolidin-1-yl)-methanone | 84.9 |
| 6-(3-Chloro-phenyl)-pyrimidine-4-carboxylicacid[4-(4-methyl-piperazin-1-yl)-phenyl]-amide | 87.7 |
| 6-(3-Chloro-phenyl)-pyrimidine-4-carboxylic acid (6-trifluoromethyl-pyridin-3-yl)-amide | 89.1 |
| 6-(3-Chloro-phenyl)-pyrimidine-4-carboxylic acid (pyridin-3-ylmethyl)-amide | 96.7 |
| 6-(3-Chloro-phenyl)-pyrimidine-4-carboxylic acid pyridazin-3-ylamide | 100.0 |
| 6-(3-Chloro-phenyl)-pyrimidine-4-carboxylic acid pyrazin-2-ylamide | 100.0 |
| 6-(3-Chloro-phenyl)-pyrimidine-4-carboxylic acid (4-morpholin-4-yl-phenyl)-amide | 93.6 |
| (S)-1-[6-(3-Chloro-phenyl)-pyrimidine-4-carbonyl]-pyrrolidine-2-carboxylic acid amide | 91.1 |
| (R)-1-[6-(3-Chloro-phenyl)-pyrimidine-4-carbonyl]-pyrrolidine-2-carboxylic acid amide | 95.4 |
| Azetidin-1-yl-[6-(3-chloro-phenyl)-pyrimidin-4-yl]-methanone | 100.0 |
| 6-(4-Methoxy-phenyl)-pyrimidine-4-carboxylic acid | 100.0 |
| [6-(3-Chloro-phenyl)-pyrimidin-4-yl]-(1,3-dihydro-isoindol-2-yl)-methanone | 100.0 |
| 6-(3-Chloro-phenyl)-pyrimidine-4-carboxylic acid (3,5-dimethyl-isoxazol-4-yl)-amide | 79.0 |
| [6-(3,4-Dichloro-phenyl)-pyrimidin-4-yl]-(3,4-dihydro-2H-quinolin-1-yl)-methanone | 92.6 |
| 6-(3,4-Dichloro-phenyl)-pyrimidine-4-carboxylic acid phenylamide | 100.0 |
| 6-(3,4-Dichloro-phenyl)-pyrimidine-4-carboxylic acid p-tolylamide | 100.0 |
| 6-(3,4-Dichloro-phenyl)-pyrimidine-4-carboxylic acid (5-methoxy-pyridin-3-yl)-amide | 100.0 |
| 6-(3,4-Dichloro-phenyl)-pyrimidine-4-carboxylic acid pyrimidin-5-ylamide | 95.5 |
| 6-(3,4-Dichloro-phenyl)-pyrimidine-4-carboxylic acid (6-methyl-pyridin-3-yl)-amide | 100.0 |

-continued

| IUPAC name | INH.Mouse @ 10 μM |
|---|---|
| 6-(3,4-Dichloro-phenyl)-pyrimidine-4-carboxylic acid (6-methyl-pyridin-3-yl)-amide hydrochloride salt | 94.0 |
| 6-(3,4-Dichloro-phenyl)-pyrimidine-4-carboxylic acid (2-methyl-pyridin-3-yl)-amide | 84.2 |
| 6-(3-Chloro-phenyl)-pyrimidine-4-carboxylic acid pyrimidin-2-ylamide | 100.0 |
| 6-(3-Chloro-phenyl)-pyrimidine-4-carboxylic acid methyl-p-tolyl-amide | 100.0 |
| 6-(3-Fluoro-phenyl)-pyrimidine-4-carboxylic acid methyl ester | 100.0 |
| 6-(3-Chloro-phenyl)-pyrimidine-4-carboxylic acid (6-methyl-pyridin-3-yl)-amide | 85.3 |
| 6-(3-Chloro-phenyl)-pyrimidine-4-carboxylic acid (2-methyl-pyridin-3-yl)-amide | 97.8 |
| 6-(3-Chloro-phenyl)-pyrimidine-4-carboxylic acid (4-fluoro-phenyl)-amide | 98.9 |
| 6-(3-Fluoro-phenyl)-pyrimidine-4-carboxylic acid | 100.0 |
| 6-(3,5-Dichloro-phenyl)-pyrimidine-4-carboxylic acid phenylamide | 77.6 |
| [6-(3,5-Dichloro-phenyl)-pyrimidin-4-yl]-(2,3-dihydro-indol-1-yl)-methanone | 98.3 |
| 6-(3,5-Dichloro-phenyl)-pyrimidine-4-carboxylic acid (5-methoxy-pyridin-3-yl)-amide | 54.8 |
| 6-(3-Chloro-phenyl)-pyrimidine-4-carboxylic acid (1-methyl-1H-pyrazol-3-yl)-amide | 100.0 |
| 6-(3-Chloro-phenyl)-pyrimidine-4-carboxylic acid (1-methyl-1H-pyrazol-4-yl)-amide | 100.0 |
| 6-(3-Chloro-phenyl)-pyrimidine-4-carboxylic acid (4-methoxy-phenyl)-methyl-amide | 100.0 |
| [6-(3-Chloro-phenyl)-pyrimidin-4-yl]-(2-methyl-2,3-dihydro-indol-1-yl)-methanone | 76.9 |
| 6-(3-Fluoro-phenyl)-pyrimidine-4-carboxylic acid pyridin-3-ylamide | 94.8 |
| 6-(3-Chloro-phenyl)-pyrimidine-4-carboxylic acid (2,2-difluoro-benzo[1,3]dioxol-5-yl)-amide | 97.7 |
| [6-(3-Chloro-phenyl)-pyrimidin-4-yl]-(5-fluoro-2,3-dihydro-indol-1-yl)-methanone | 100.0 |
| (5-Chloro-2,3-dihydro-indol-1-yl)-[6-(3-chloro-phenyl)-pyrimidin-4-yl]-methanone | 100.0 |
| 6-(3-Chloro-4-trifluoromethyl-phenyl)-pyrimidine-4-carboxylic acid methyl ester | 100.0 |
| 6-(3-Chloro-4-trifluoromethyl-phenyl)-pyrimidine-4-carboxylic acid | 100.0 |
| 6-(3-Chloro-4-trifluoromethyl-phenyl)-pyrimidine-4-carboxylic acid pyridin-3-ylamide | 48.3 |
| [6-(3-Chloro-phenyl)-pyrimidin-4-yl]-(2,3-dihydro-pyrrolo[3,2-c]pyridin-1-yl)-methanone | 100.0 |
| 6-(3-Chloro-phenyl)-pyrimidine-4-carboxylic acid (2,2-difluoro-benzo[1,3]dioxol-5-yl)-methyl-amide | 98.7 |
| 6-(3-Chloro-phenyl)-pyrimidine-4-carboxylic acid thiazol-2-ylamide | 100.0 |
| 6-(3-Chloro-phenyl)-pyrimidine-4-carboxylic acid (3-methyl-isoxazol-5-yl)-amide | 100.0 |
| 6-(3-Chloro-phenyl)-pyrimidine-4-carboxylic acid (5-methyl-[1,3,4]oxadiazol-2-yl)-amide | 100.0 |
| 6-(3-Chloro-phenyl)-pyrimidine-4-carboxylic acid oxazol-2-ylamide | 100.0 |
| 6-(3-Chloro-phenyl)-pyrimidine-4-carboxylic acid (3-methyl-[1,2,4]thiadiazol-5-yl)-amide | 85.4 |
| 6-(3,4-Difluoro-phenyl)-pyrimidine-4-carboxylic acid methyl ester | 100.0 |
| 6-(5-Chloro-2-fluoro-phenyl)-pyrimidine-4-carboxylic acid methyl ester | 100.0 |
| 6-(3,4-Difluoro-phenyl)-pyrimidine-4-carboxylic acid | 100.0 |
| 6-(3,4-Difluoro-phenyl)-pyrimidine-4-carboxylic acid pyrimidin-5-ylamide | 100.0 |
| 6-(5-Chloro-2-fluoro-phenyl)-pyrimidine-4-carboxylic acid | 100.0 |
| [6-(3,4-Dichloro-phenyl)-pyrimidin-4-yl]-(1',2'-dihydro-spiro[cyclopropane-1,3'-[3H]indol]-1')-methanone | 100.0 |
| 6-(3,4-Dichloro-phenyl)-pyrimidine-4-carboxylic acid (2,6-dimethyl-pyridin-3-yl)-amide | 96.8 |
| 6-(3,4-Dichloro-phenyl)-pyrimidine-4-carboxylic acid (3-methyl-isoxazol-5-yl)-amide | 100.0 |
| 6-(3-Chloro-4-fluoro-phenyl)-pyrimidine-4-carboxylic acid methyl ester | 100.0 |
| 6-(3,4-Dichloro-phenyl)-pyrimidine-4-carboxylic acid (5-methyl-[1,3,4]oxadiazol-2-yl)-amide | 100.0 |
| 6-(3-Chloro-4-methoxy-phenyl)-pyrimidine-4-carboxylic acid methyl ester | 100.0 |
| 6-(3-Chloro-4-methoxy-phenyl)-pyrimidine-4-carboxylic acid | 100.0 |
| 6-(3,4-Dichloro-phenyl)-pyrimidine-4-carboxylic acid (pyridin-4-ylmethyl)-amide | 95.5 |
| 6-(3-Chloro-4-fluoro-phenyl)-pyrimidine-4-carboxylic acid | 100.0 |
| 6-(3,4-Dichloro-phenyl)-5-fluoro-pyrimidine-4-carboxylic acid methyl ester | 100.0 |
| 6-(3,4-Dichloro-phenyl)-pyrimidine-4-carboxylic acid [1,3,4]thiadiazol-2-ylamide | 100.0 |

-continued

| IUPAC name | INH.Mouse @ 10 µM |
|---|---|
| (5-Chloro-2,3-dihydro-indol-1-yl)-[6-(3,4-dichloro-phenyl)-pyrimidin-4-yl]-methanone | 100.0 |
| [6-(3,4-Dichloro-phenyl)-pyrimidin-4-yl]-(5-fluoro-2,3-dihydro-indol-1-yl)-methanone | 100.0 |
| 6-(3,4-Dichloro-phenyl)-5-fluoro-pyrimidine-4-carboxylic acid | 100.0 |
| 6-(3,4-Dichloro-phenyl)-pyrimidine-4-carboxylic acid pyridin-4-ylamide | 90.1 |
| 6-(3,4-Dichloro-phenyl)-pyrimidine-4-carboxylic acid pyridin-2-ylamide | 100.0 |
| 6-(3,4-Dichloro-phenyl)-pyrimidine-4-carboxylic acid (1-methyl-1H-pyrazol-4-yl)-amide | 100.0 |
| 6-(3,4-Dichloro-phenyl)-pyrimidine-4-carboxylic acid isoxazol-3-ylamide | 100.0 |
| 6-(3,4-Dichloro-phenyl)-pyrimidine-4-carboxylic acid thiazol-2-ylamide | 83.7 |
| [6-(3,4-Dichloro-phenyl)-pyrimidin-4-yl]-(1,3-dihydro-isoindol-2-yl)-methanone | 63.5 |
| 6-(3,4-Difluoro-phenyl)-pyrimidine-4-carboxylic acid pyridin-3-ylamide | 84.7 |
| 6-(3,4-Dichloro-phenyl)-pyrimidine-4-carboxylic acid (2-methyl-pyrimidin-5-yl)-amide | 85.6 |
| 2-(3-Chloro-phenyl)-isonicotinic acid hydrochloride salt | 53.5 |
| 4-(3-Chloro-phenyl)-pyridine-2-carboxylic acid | 100.0 |
| 4-(3-Chloro-phenyl)-pyridine-2-carboxylic acid methyl ester | 100.0 |
| 4-(3-Chloro-phenyl)-pyridine-2-carboxylic acid pyridin-3-ylamide | 52.3 |
| 4-(3-Chloro-phenyl)-pyridine-2-carboxylic acid phenylamide | 68.4 |
| [4-(3-Chloro-phenyl)-pyridin-2-yl]-(2,3-dihydro-indol-1-yl)-methanone | 100.0 |
| 4-(3-Chloro-phenyl)-pyridine-2-carboxylic acid p-tolylamide | 85.6 |
| 4-(3-Chloro-phenyl)-pyridine-2-carboxylic acid (5-methoxy-pyridin-3-yl)-amide | 53.8 |
| 4-(3,5-Dichloro-phenyl)-pyridine-2-carboxylic acid phenylamide | 59.7 |
| 4-(3,5-Dichloro-phenyl)-pyridine-2-carboxylic acid (5-methoxy-pyridin-3-yl)-amide | 52.6 |
| [4-(3,5-Dichloro-phenyl)-pyridin-2-yl]-(2,3-dihydro-indol-1-yl)-methanone | 54.5 |
| 4-(3-Chloro-phenyl)-pyridine-2-carboxylic acid pyrimidin-5-ylamide | 60.8 |
| 4-(3,4-Dichloro-phenyl)-pyridine-2-carboxylic acid phenylamide | 43.5 |
| [4-(3,4-Dichloro-phenyl)-pyridin-2-yl]-(2,3-dihydro-indol-1-yl)-methanone | 96.6 |
| 4-(3,4-Dichloro-phenyl)-pyridine-2-carboxylic acid hydrochloride salt | 100.0 |
| 4-(3,5-Dichloro-phenyl)-pyridine-2-carboxylic acid hydrocloride salt | 76.6 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:
1. At least one chemical entity chosen from compounds of Formula I

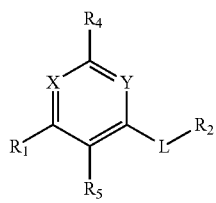

Formula I and pharmaceutically acceptable salts thereof wherein:
X and Y are N;

$R_1$ is phenyl optionally substituted with one, two, or three groups chosen from halo, optionally substituted lower alkyl, lower alkoxy, and hydroxy;
L is chosen from —C(O)O—, N($R_3$)C(O)—, and —S(O)$_2$N($R_3$)—;
$R_2$ is hydrogen;
$R_3$ is chosen from hydrogen and lower alkyl;
$R_4$ is hydrogen; and
$R_5$ is chosen from hydrogen and fluoro,
provided that the compound of Formula I is not
6-(4-methoxy-phenyl)-pyrimidine-4-carboxylic acid;
6-(3,4-Dichloro-phenyl)-2-methyl-pyrimidine-4-carboxylic acid;
or 6-phenylpyrimidine-4-carboxylic acid.

2. At least one chemical entity of claim 1 wherein $R_1$ is phenyl optionally substituted with one, two, or three groups chosen from halo, lower alkyl, trifluoromethyl, lower alkoxy, and hydroxy.

3. At least one chemical entity of claim 2 wherein $R_1$ is phenyl optionally substituted with one, two, or three groups chosen from halo, lower alkyl, and trifluoromethyl.

4. At least one chemical entity of claim 3 wherein $R_1$ is chosen from 2-trifluoromethylphenyl, 3,4-dichlorophenyl, 3-chlorophenyl, 4-chlorophenyl, and 3,5-dichlorophenyl.

5. At least one chemical entity of claim 1 wherein L is —C(O)O—.

6. At least one chemical entity of claim 1 wherein $R_5$ is hydrogen.

* * * * *